(12) United States Patent
Lee et al.

(10) Patent No.: US 11,491,235 B2
(45) Date of Patent: Nov. 8, 2022

(54) ORAL GENE CARRIER AND USE THEREOF

(71) Applicant: KB BIOMED INC., Chungcheongbuk-do (KR)

(72) Inventors: Yong Kyu Lee, Chungcheongbuk-do (KR); Seung Bin Cha, Gyeonggi-do (KR); Sung Hun Kang, Chungcheongbuk-do (KR); Sun Hwa Lee, Daejeon (KR)

(73) Assignee: KB BIOMED INC., Chungcheongbuk-do (KR)

( * ) Notice: Subject to any disclaimer, the term of this patent is extended or adjusted under 35 U.S.C. 154(b) by 80 days.

(21) Appl. No.: 16/956,779

(22) PCT Filed: Dec. 20, 2018

(86) PCT No.: PCT/KR2018/016312
§ 371 (c)(1),
(2) Date: Aug. 20, 2020

(87) PCT Pub. No.: WO2019/125003
PCT Pub. Date: Jun. 27, 2019

(65) Prior Publication Data
US 2020/0390897 A1    Dec. 17, 2020

(30) Foreign Application Priority Data

Dec. 22, 2017 (KR) .................. 10-2017-0177672
Dec. 22, 2017 (KR) .................. 10-2017-0177673
Dec. 22, 2017 (KR) .................. 10-2017-0177675

(51) Int. Cl.
| | |
|---|---|
| A61K 47/64 | (2017.01) |
| A61K 47/54 | (2017.01) |
| A61K 9/00 | (2006.01) |
| A61K 38/17 | (2006.01) |
| A61K 38/26 | (2006.01) |
| A61K 48/00 | (2006.01) |

(52) U.S. Cl.
CPC ............ *A61K 47/64* (2017.08); *A61K 9/0053* (2013.01); *A61K 38/17* (2013.01); *A61K 38/26* (2013.01); *A61K 47/549* (2017.08); *A61K 48/00* (2013.01)

(58) Field of Classification Search
CPC ....... A61K 47/64; A61K 9/0053; A61K 38/26
See application file for complete search history.

(56) References Cited

U.S. PATENT DOCUMENTS 7,452,966 B2   11/2008   Glaesner et al.
2011/0091543 A1*  4/2011   Prior .................... A61K 47/644
                                                              424/463
2014/0113370 A1   4/2014   Camphausen et al.

FOREIGN PATENT DOCUMENTS

KR    10-2016-0083810 A    7/2016
KR    10-2017-0106258 A    9/2017

OTHER PUBLICATIONS

Chen, et al. (2013) "Fusion protein linkers: Property, design and functionality." *Advanced Drug Delivery Reviews*, 65:1357-1369.
Mie Kristensen & Hanne Mørck Nielsen (2016) "Cell-penetrating peptides as tools to enhance non-injectable delivery of biopharmaceuticals." *Tissue Barriers*, 4:2, e1178369, 15 pages. DOI: 10.1080/21688370.2016.1178369.
Soltani, et al. (2007) "In vivo expression of GLP-1/IgG-Fcfusion protein enhances beta-cell mass and protects against streptozotocin-induced diabetes." *Gene Therapy*, 14:981-988.
International Search Report dated Apr. 16, 2019, issued in International Patent Application No. PCT/KR2018/016312, with English translation.

* cited by examiner

*Primary Examiner* — Gyan Chandra
(74) *Attorney, Agent, or Firm* — Harness, Dickey & Pierce, P.L.C.

(57) ABSTRACT

The present invention relates to an orally-administered gene carrier and a use thereof, and more specifically, to: an oral gene carrier comprising, at the C-terminus of an immunoglobulin Fc region, a linker formed from cationic arginine and enabling the condensation of an anionic gene; and an oral composition for preventing, ameliorating or treating metabolic diseases, the composition comprising the gene carrier and the GLP-1 gene as active ingredients. The gene carrier, according to the present invention, may be usefully employed as an orally-administered carrier for various genes, and especially, is expected to be usable for preventing, ameliorating or treating metabolic diseases, such as diabetes and obesity, by effectively transferring the GLP-1 gene.

10 Claims, 22 Drawing Sheets
Specification includes a Sequence Listing.

ORAL GENE CARRIER AND USE THEREOF

CROSS-REFERENCE TO RELATED APPLICATIONS

This application is a national phase application of PCT Application No. PCT/KR2018/016312, filed 20 Dec. 2018, which claims benefit of Korean Patent Application No. 10-2017-0177672, filed on Dec. 22, 2017, Korean Patent Application No. 10-2017-0177673, filed on Dec. 22, 2017 and Korean Patent Application No. 10-2017-0177675, filed on Dec. 22, 2017. The entire disclosures of the applications identified in this paragraph are incorporated herein by references.

FIELD

The present invention relates to an orally-administered gene carrier and a use thereof, and more specifically, to: an oral gene carrier comprising, at the C-terminus of an immunoglobulin Fc region, a linker formed from cationic arginine and enabling the condensation of an anionic gene; and an oral composition for preventing, ameliorating or treating metabolic diseases, the composition comprising the gene carrier and the GLP-1 gene as active ingredients.

BACKGROUND

Diabetes mellitus, which is known as a representative metabolic disease, is a metabolic disease occurring due to the absence of insulin secretion or action, and is characterized by hyperglycemia. Diabetes mellitus may be roughly divided into type 1 and type 2, type 1 diabetes mellitus is caused by the destruction of β cells in the pancreas by autoimmune mechanisms, viral infections, and the like, and in the case of type 2 diabetes mellitus (abbreviation: T2DM), a reduction in insulin secretion and the insulin resistance to insulin action in target organs such as liver, adipose tissues, and muscle are said to be representative causes. Type 2 diabetes mellitus may be partially improved through exercise therapy, weight loss, and the like, but it is difficult to easily improve type 1 diabetes mellitus due to a reduction in insulin secretion ability, so that a means to supplement insulin from the outside is used.

Drugs currently used to treat type 2 diabetes mellitus include insulin agents and hypoglycemic agents, and the most commonly used oral hypoglycemic agents include biguanide which suppresses the synthesis of glucose in the liver, sulfonylurea and glinide which promote insulin secretion by β cells, thiazolidinedione which is an insulin sensitizer, and the like. However, despite combined treatment of these drugs, about ⅓ of patients can regulate blood sugar below the target level, and these hypoglycemic agents or insulin cannot ameliorate or completely treat diabetes mellitus. In addition, the current therapeutic agents for diabetes mellitus are therapeutic agents which are continuously administered because the therapeutic agents have problems such as side effects including induction of hypoglycemia, gastrointestinal disturbances, diarrhea, liver and cardiotoxicity, and the like, so that there is a problem in that strict management is required.

Obesity occurs when adipose tissues in the body are in excess and the amount of calories ingested is greater than the amount of calories consumed, and also occurs due to various causes such as mental and social factors, genetics, diseases, and drugs. According to the World Health Organization (WHO) in 2010, it was reported that the overweight adult population was estimated at about 1.6 billion worldwide and the number of obese people was estimated at about 400 million, and 2.6 million people die from obesity or overweight every year. Even in Korea, according to the reports by the Ministry of Health and Welfare and the Korea Centers for Disease Control & Prevention, adult obesity rates have continued to increase, and were shown to be 30% (36.3% male, 24.8% female) based on the year 2010. As described above, the obese population continues to increase worldwide, and the burden of medical expenses is also increasing.

The severity of obesity is more recognized due to various complications which may be induced by obesity than its own risks. Obesity is known to increase the risk of a metabolic syndrome such as hypertension, hyperlipidemia, and diabetes mellitus, fatty liver, dysarthrosis, and cancer development. According to an announcement released by the World Health Organization in 2010, the risk of hypertension, diabetes mellitus, dyslipidemia, and the like in obese people is shown to be twice or more as high as that of people with normal body weight (2.5 times higher for hypertension, 2 times higher for diabetes mellitus, 2.3 times higher for hypercholesterolemia, and 2.4 times higher for hypertriglyceridemia). It is known that in addition to the above diseases, when the body fat of a woman is too high, the balance of sex hormones is lost, and when the body fat is severe, the body fat may cause infertility, and increases the risk of endometrial cancer and breast cancer. In addition, since obesity may induce not only physical diseases but also mental diseases such as social isolation or alienation, lack of self-confidence, and depression, the need for preventing and treating obesity is recognized to be very important.

Obesity may be treated through improvement in lifestyles such as behavioral therapy along with dietary therapy and regular exercise, and drugs such as appetite suppressants and fat absorption inhibitors. Since obesity is a chronic disease, long-term use of medication is required when drug therapy is attempted, and currently, products that have been approved for long-term use in Korea for three or more months include sibutramine as an appetite suppressant and orlistat as a lipase inhibitor. However, since most of these drugs for treating obesity are psychotropic drugs that act on the central nervous system to regulate appetite, these drugs are accompanied by side effects such as headaches and vomiting, and have problems such as concerns of abuse. Therefore, studies have been actively conducted to develop a material having high safety, which can solve the side effects of the aforementioned commercially available anti-obesity agents, and having an excellent anti-obesity effect.

Examples of a representative method which may be used to solve such a problem include a therapeutic method using nucleic acid delivery, examples of a method therefor include a method using a viral vector and a method using a non-viral vector. However, since the viral vector uses a carrier extracted from a virus as a raw material, there is a limitation in applying the viral vector in vivo, so that studies have been conducted as a method using a vector based on a polymer which is a non-viral vector. This method basically includes cationic compounds such as polymers, lipids, or inorganic materials, which are capable of binding or adsorbing negatively charged DNA to nano-sized particles. Further, a gene therapeutic method using such a nucleic acid carrier has been highlighted as a promising method for preventing and treating T2MD by treating the origin of T2MD.

Meanwhile, in gene therapy, it is known that a method by oral gene delivery can provide several advantages. First, gene therapy can provides the patient with the convenience because they can avoid injections, and second, gene therapy can deliver a gene to the intestinal epithelial cells using a shorter distance than a method of passing through the blood, so that it is advantageous to maintain the stability of a gene and express the gene after delivery. In addition, an effective oral gene delivery system may be used for systemic delivery of protein drugs because the effective oral delivery system can induce the circulation of proteins by expression and secretion of therapeutic proteins in epithelial cells. Although the concept of oral gene therapy has already been proved, non-viral gene delivery through an intestinal segment has a problem of low expression levels, which suffers from many difficulties. Furthermore, there remains a challenge of effectively controlling the degradation by intestinal enzymes, microorganisms, and digestive juices. However, a carrier preparation by an Fc receptor (FcRn) has the ability to pass through the intestinal epithelial cells, so that it is possible to solve the aforementioned problems due to uptake efficiency.

An Fc region of an antibody serves to recruit immune leukocytes or serum complement molecules, thereby allowing damaged cells such as cancer cells or infected cells to be removed. The site on Fc between the Cγ2 and Cγ3 domains mediates the interaction with a neonatal receptor FcRn and this binding recirculates an intracellularly introduced antibody from an endosome to the bloodstream. This process is associated with the inhibition of kidney filtration due to the enormous size of a full-length molecule, thereby having an advantageous antibody serum half-life ranging from 1 to 3 weeks. Further, the binding of Fc to FcRn also plays an important role in antibody transfer. Therefore, the Fc region plays an essential role in maintaining the prolonged serum persistence of an antibody because the antibody is circulated through an intracellular trafficking and recycling mechanism. Accordingly, in many ongoing clinical studies, many efforts have been made to introduce mutations into an Fc region in order to increase the half-life of the antibody, or to develop a next-generation anticancer antibody therapeutic agent or an anticancer protein therapeutic agent through an Fc domain into which mutations are introduced in order to maximize an antibody-dependent cellular cytotoxicity (ADCC) effect. However, the results are still incomplete.

Referring to American Diabetes Association (ADA) guidelines, a drug, which is primarily selected, is metformin, secondary and tertiary drugs are sulfonylurea-based drugs, glinide-based drugs, and thiazolidinedione-based drugs, DPP-4 inhibitors, and the like, and thereafter, an injection such as glucagon like peptide-1 (GLP-1) agonist or an insulin injection has been used. However, in the case of existing oral diabetes therapeutic agents currently used in clinical practice, in addition to the positive aspect of maintenance of sustained normalization of blood sugar, long term use causes various side effects such as induction of hypoglycemia, diarrhea, body weight gain, problems with the cardiovascular system, and liver toxicity and ultimately, the β cells of the pancreas are destroyed, and insulin needs to be finally injected. In addition, since insulin administration, which is the final treatment method, also needs to subcutaneously inject insulin two to three times daily, the method is uncomfortable and is likely to induce hypoglycemia, which is the greatest side effect.

Glucagon-like peptide-1 (GLP-1) has recently been in the limelight as a next-generation diabetes therapeutic agent to compensate for these problems. GLP-1 and analogs and derivatives thereof show good potential in clinical trials for the treatment of type 2 diabetes mellitus, and induce numerous biological effects such as stimulation of insulin secretion, inhibition of glucagon secretion, inhibition of gastric emptying, inhibition of gastric or intestinal motility, and induction of weight loss. Further, GLP-1 and analogs and derivatives thereof have a pancreatic protective function even when GLP-1 and analogs and derivatives thereof are taken for a long period of time, have no risk of hypoglycemia, and can maintain suitable blood sugar for a long period of time.

In addition, it is known that the secretion of GLP-1 is stimulated by activation of TGR5 and GPR119, which are types of G protein-coupled receptors (GPCRs), or activation of α-gustducin. In particular, activation of G protein-coupled receptor (GPCR) TGR5 (GPR131) expressed in brown adipose tissue and muscle exhibits an effect of treating obesity by increasing energy consumption, is known to be associated with amelioration of liver diseases, and is reported to inhibit arteriosclerosis.

However, in vivo, the GLP-1 is cleaved and inactivated by an enzyme called DPP-4, and thus has a very short in vivo half-life, which makes it difficult to be developed as a therapeutic agent, so that various approach methods have been conducted in order to prolong the half-life of GLP-1 or reduce the rate of peptide removal from the body while maintaining biological activity. That is, various GLP-1 analogs as described above have been actively developed, and an approach of fusing GLP-1 to an immunoglobulin Fc region has been attempted (U.S. Pat. No. 7,452,966 B2), but the technology has not progressed sufficiently.

SUMMARY

Technical Problem

The present invention has been devised to solve the problems as described above, and as a result of intensive studies on a carrier for efficiently delivering a gene into human somatic cells, it was confirmed that a gene carrier which enables nine arginines, which are amino acids having cationic properties, to bind to the C-terminus of an immunoglobulin Fc region in order to effectively condense a gene having anionic properties was stable against pH and systemic enzymes, and its usability as an orally-administered gene carrier was confirmed, and thus based on this, the present invention was completed.

Thus, an object of the present invention is to provide an orally-administered gene carrier including: an immunoglobulin Fc region; and a linker linked to the C-terminus of the immunoglobulin Fc region.

Further, another object of the present invention is to provide a method for preparing the gene carrier.

In addition, still another object of the present invention is to provide an oral composition for preventing or treating metabolic diseases, the composition comprising the gene carrier and a glucagon like peptide-1 (GLP-1) gene bound to the carrier as active ingredients.

However, technical problems to be achieved by the present invention are not limited to the aforementioned problems, and other problems that are not mentioned may be clearly understood by those skilled in the art from the following description.

Technical Solution

To achieve the objects as described above, the present invention provides an orally-administered gene carrier including:
an immunoglobulin Fc region; and
a linker linked to the C-terminus of the immunoglobulin Fc region.

As an exemplary embodiment of the present invention, the orally-administered gene carrier may include an amino acid sequence of SEQ ID NO: 1.

As another exemplary embodiment of the present invention, the orally-administered gene carrier may include a base sequence of SEQ ID NO: 2.

As still another exemplary embodiment of the present invention, the immunoglobulin Fc region may include an amino acid sequence of SEQ ID NO: 3.

As yet another exemplary embodiment of the present invention, the immunoglobulin Fc region may include a base sequence of SEQ ID NO: 4.

As yet another exemplary embodiment of the present invention, the immunoglobulin Fc region may be derived from any one selected from the group consisting of IgG, IgA, IgD, IgE, and IgM.

As yet another exemplary embodiment of the present invention, the immunoglobulin Fc region may be derived from IgG.

As yet another exemplary embodiment of the present invention, the linker may include an amino acid sequence of Arg-Arg-Arg-Arg-Arg-Arg-Arg-Arg-Arg (SEW ID NO: 6).

As yet another exemplary embodiment of the present invention, the gene carrier may be prepared by being mixed with a gene at a weight ratio (w/w) of 20:1 to 150:1.

Further, the present invention provides a method for preparing the orally-administered gene carrier, the method comprising the following steps:

(a) constructing a recombinant expression vector including a nucleic acid sequence encoding a gene carrier including an immunoglobulin Fc region and a linker linked to the C-terminus of the immunoglobulin Fc region;

(b) transforming a host cell with the expression vector and culturing the host cell; and (c) purifying an hIgG1-Fc-9Arg gene carrier expressed from the host cell and obtaining the hIgG1-Fc-9Arg gene carrier.

In addition, the present invention provides an oral composition for preventing or treating metabolic diseases, the composition comprising the gene carrier and a glucagon like peptide-1 (GLP-1) gene bound to the carrier as active ingredients.

As an exemplary embodiment of the present invention, the GLP-1 may include a base sequence of SEQ ID NO: 5.

As another exemplary embodiment of the present invention, the metabolic disease may be selected from the group consisting of obesity, diabetes mellitus, dyslipidemia, insulin resistance, hepatic steatosis, hypercholesterolemia, and non-alcoholic fatty liver.

Furthermore, the present invention provides a method for treating metabolic diseases, the method including: administering the oral composition to an individual.

Further, the present invention provides a use of the composition for preventing or treating metabolic diseases.

Advantageous Effects

The orally-administered gene carrier of the present invention can effectively induce gene expression in vivo by binding nine arginines which are amino acids having cationic properties to the C-terminus of an Fc portion to achieve condensation with a gene having anionic properties, and also, a gene can be delivered to the small intestine by protecting the gene from a degradation action caused by an immune action of gastric acid and leukocytes during oral administration, and when the gene is expressed in the small intestine, a long-term treatment effect possibility was confirmed due to the relatively long half-life, so that the gene carrier according to the present invention can be usefully employed as an orally-administered carrier for various genes, and especially, is expected to be usable for preventing, ameliorating or treating metabolic diseases, such as diabetes and obesity, by effectively delivering the GLP-1 gene.

DETAILED DESCRIPTION

Figure 1A:
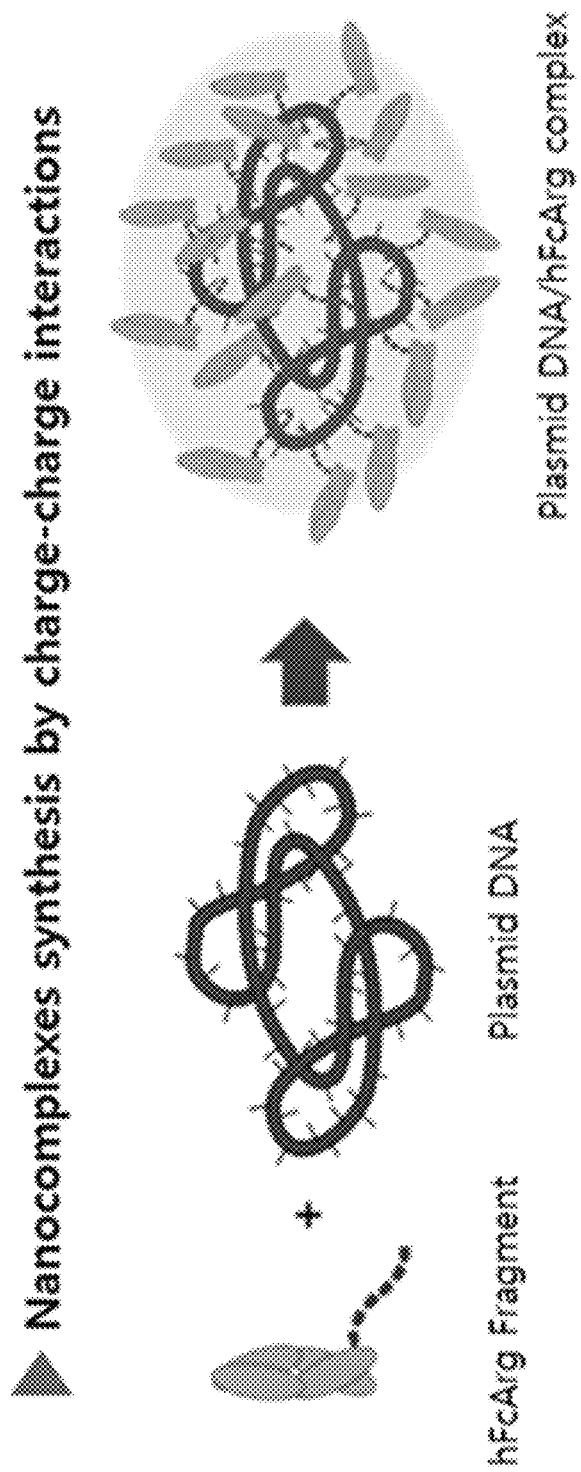
FIG. 1A illustrates a complex formation process of antibody hIgG1-Fc-9Arg and plasmid DNA (pDNA) with drawings.

Hereinafter, the present invention will be described in detail.

As a result of intensive studies on a carrier for efficiently delivering a gene into body cells, the present inventors confirmed that a gene carrier which enables nine arginines, which are amino acids having cationic properties, to bind to the C-terminus of an Fc portion in order to effectively condense a gene having cationic properties was stable against pH and systemic enzymes, and confirmed its usability as an orally-administered carrier, thereby completing the present invention.

Thus, the present invention provides an orally-administered gene carrier including: an immunoglobulin Fc region; and a linker linked to the C-terminus of the immunoglobulin Fc region.

In the present invention, the orally-administered gene carrier may include an amino acid sequence of SEQ ID NO: 1, and a gene encoding the same may include a base sequence of SEQ ID NO: 2. In this case, the orally-administered gene carrier may include an amino acid sequence or a base sequence, which has a sequence homology of 70% or more, preferably 80% or more, more preferably 90% or more, even more preferably 95% or more, and most preferably 98% or more with the amino acid sequence represented by SEQ ID NO: 1 or the base sequence represented by SEQ ID NO: 2, respectively.

As used herein, the term "immunoglobulin Fc region" refers to heavy chain constant region 2 (CH2) and heavy chain constant region 3 (CH3) portions, excluding heavy and light chain variable regions, a heavy chain constant region 1 (CH1) and a light chain constant region 1 (CL1) of an immunoglobulin, and also includes a hinge portion in the heavy chain constant region. Further, the immunoglobulin Fc region of the present invention may be an extended Fc region including a part or the entirety of the heavy chain constant region 1 (CH1) and/or the light chain constant region 1 (CL1), excluding the heavy and light chain variable regions of the immunoglobulin, as long as the immunoglobulin Fc region of the present invention has substantially the same effect as or an improved effect compared to that of a natural type. In addition, the immunoglobulin Fc region may also be a region in which a significantly long partial amino acid sequence corresponding to CH2 and/or CH3 is removed.

Furthermore, the immunoglobulin Fc region of the present invention includes not only a natural-type amino acid sequence but also a sequence derivative (mutant) thereof. An amino acid sequence derivative means that one or more amino acid residues in a natural amino acid sequence have different sequences due to deletion, insertion, non-conservative or conservative substitution, or a combination thereof.

In the present invention, the immunoglobulin Fc region may include an amino acid sequence of SEQ ID NO: 3, and a gene encoding the same may include a base sequence of SEQ ID NO: 4. In this case, the immunoglobulin Fc region may include an amino acid sequence or a base sequence, which has a sequence homology of 70% or more, preferably 80% or more, more preferably 90% or more, even more preferably 95% or more, and most preferably 98% or more with the amino acid sequence represented by SEQ ID NO: 3 or the base sequence represented by SEQ ID NO: 4, respectively.

Furthermore, these Fc regions may be obtained from a natural type isolated in vivo from an animal such as a human, a cow, a goat, a pig, a mouse, a rabbit, a hamster, a rat, or a guinea pig, and may be a recombinant type obtained from transformed animal cells or microorganisms, or a derivative thereof. Here, the method of obtaining an Fc region from a natural type may be a method of obtaining an Fc region by isolating an entire immunoglobulin from a human or animal organism and then treating the entire immunoglobulin with a proteolytic enzyme. When the immunoglobulin is treated with papain, the immunoglobulin is cleaved into Fab and Fc, and when the immunoglobulin is treated with pepsin, the immunoglobulin is cleaved into pF'c and F(ab)2. Fc or pF'c may be isolated from the cleaved portions using size exclusion chromatography, and the like. In the present invention, the immunoglobulin Fc region is a recombinant type immunoglobulin Fc region, preferably, a human-derived Fc region obtained from a microorganism.

Further, the immunoglobulin Fc region may be a natural sugar chain, an increased sugar chain compared to the natural type, a decreased sugar chain compared to the natural type, or a form in which a sugar chain is removed. In order to increase/decrease or remove the immunoglobulin Fc sugar chains, a typical method such as a chemical method, an enzymatic method, and a genetic engineering method using microorganisms may be used. Here, the immunoglobulin Fc region in which the sugar chain is removed from Fc does not cause unnecessary immune reactions in vivo, because the binding power to a complement (c1q) is remarkably reduced, and antibody-dependent cytotoxicity or complement-dependent cytotoxicity is reduced or removed. In this regard, a form which is more consistent with the intended purpose as a drug carrier may be said to be an immunoglobulin Fc region in which the sugar chain has been removed or deglycosylated.

In addition, the immunoglobulin Fc region may be an Fc region derived from IgG, IgA, IgD, IgE, IgM, or a combination thereof or a hybrid thereof, and is most preferably derived from IgG known to improve the half-life of a ligand-binding protein most abundant in human blood.

In the present invention, an amino acid as a linker having cationic properties in order to effectively condense a gene having anionic properties is bound to the C-terminal of an immunoglobulin Fc region, and the linker may include an amino acid sequence of Arg-Arg-Arg-Arg-Arg-Arg-Arg-Arg-Arg (SEQ ID NO: 6), but is not limited thereto.

In the present invention, the gene carrier may be prepared by being mixed with a gene at a weight ratio (w/w) of 20:1 to 150:1, more preferably at a weight ratio (w/w) of 20:1 to 100:1, and even more preferably at a weight ratio (w/w) of 50:1 to 100:1.

Thus, as another aspect of the present invention, the present invention provides a method for preparing the orally-administered gene carrier, the method comprising the following steps:

(a) constructing a recombinant expression vector including a nucleic acid sequence encoding a gene carrier including an immunoglobulin Fc region and a linker linked to the C-terminus of the immunoglobulin Fc region;

(b) transforming a host cell with the expression vector and culturing the host cell; and (c) purifying an hIgG1-Fc-9Arg gene carrier expressed from the host cell and obtaining the hIgG1-Fc-9Arg gene carrier.

In exemplary embodiments of the present invention, in vitro and in vivo analyses were performed in order to confirm the characteristics of a gene carrier prepared by the method and verify its usability as an oral gene carrier.

In an exemplary embodiment of the present invention, a gene carrier of hIgG1-Fc-9Arg including the linker 9Arg and an immunoglobulin Fc region was recombined, and the characteristics of the recombined gene carrier were confirmed (see Example 2).

Furthermore, in another exemplary embodiment of the present invention, it was intended to confirm the characteristics of a complex in which the gene carrier of hIgG1-Fc-9Arg and DNA were fused. More specifically, as a result of analyzing agarose gel electrophoresis, AFM and TEM images in order to confirm whether hgG1-Fc-9Arg could be used as an efficient gene carrier, it was specifically confirmed that an anionic gene was efficiently condensed while cationic properties were increased due to the hIgG1-Fc-9Arg mass ratio, and stability against acids and enzymes was specifically confirmed (see Example 3).

Furthermore, in still another exemplary embodiment of the present invention, it was intended to confirm the gene delivery efficiency of an hIgG1-Fc-9Arg/pDNAcomplex in cells. More specifically, Caco-2 and HT-29 cell lines were selected from Caco-2, HT-29, HEK 293, HEK 293-FcRn, and HeLa cell lines by an analysis for selecting a cell line which expresses an FcRn receptor in cells, and it was confirmed through confocal microscopy that the hIgG1-Fc-9Arg/pDNA complex was delivered into cells to form endosomes. Further, in order to verify whether hIgG1-Fc-9Arg, which is an antibody-derived carrier, efficiently delivers a gene into cells, it was confirmed whether the gene was expressed in the cells by binding Bobo-3 (Ex=570 nm, Em=602 nm) to pDNA, and the gene delivery effect can be exhibited only when the antibody-derived carrier binds to the FcRn receptor of small intestinal epithelial cells and passes through the epithelial cell membrane, so that an ability to permeate cells was confirmed by performing a cell membrane permeability experiment using a Caco-2 cell monolayer membrane. In addition, as a result of confirming cell viability for the Caco-2 cell line in order to confirm whether the antibody-derived carrier can be suitably used as a safe carrier, the safety as a carrier was confirmed by confirming a cell survival of 90% or more (see Examples 4-1 to 4-5).

In yet another exemplary embodiment of the present invention, it was intended to confirm the organ specificity of the gene carrier according to the present invention using an animal model, and as a result of analyzing fluorescence imaging after a fluorescent material FITC was bound to hIgG1-Fc-9Arg and orally administered to mice, it was confirmed that IgG1-Fc-9Arg was delivered through binding to an FcRN receptor expressed in the organ, and it was confirmed that hgG1-Fc-9Arg was highly absorbed in the kidneys, liver, stomach, duodenum, jejunum, and colon (see Example 4-6).

The results confirmed that the orally-administered gene carrier according to the present invention is stable against pH and enzymes and is absorbed in various organs, and the uptake rate is high in intestinal organs, so that hIgG1-Fc-9Arg has excellent binding power to various organs, and thus based on this, is expected to exhibit an efficient ability when used as a gene carrier. Furthermore, it is suggested that the orally-administered gene carrier according to the present invention can be applied as a carrier of various genes in the future.

Thus, as still another aspect of the present invention, the present invention provides an oral composition for preventing or treating metabolic diseases, the composition comprising the gene carrier and a glucagon like peptide-1 (GLP-1) gene bound to the carrier as active ingredients.

As used herein, the term "metabolic disease" is also called a metabolic syndrome, and refers to a set of abnormal states such as an increase in body fat, an increase in blood pressure, an increase in blood sugar, and abnormal lipids in blood, which increase the risk of cerebral cardiovascular diseases and diabetes mellitus. The metabolic disease is not a single disease but a comprehensive disease caused by genetic predisposition and environmental factors, and in the present invention, may be selected from the group consisting of obesity, diabetes mellitus, dyslipidemia, insulin resistance, hepatic steatosis, hypercholesterolemia, and non-alcoholic fatty liver, and may be more preferably obesity or diabetes mellitus, but is not limited thereto.

As used herein, the term "diabetes mellitus", as a type of metabolic disease such as an insufficient amount of insulin secreted or absence of normal function, is characterized by high blood sugar with high blood glucose concentration, and causes various symptoms and signs due to hyperglycemia and releases glucose from urine. Diabetes mellitus includes type 1 diabetes mellitus which occurs when insulin is not secreted largely due to the destruction of pancreatic beta cells, and type 2 diabetes mellitus caused by insufficient insulin secretion in the body or insulin resistance in which cells do not respond to insulin. In the present invention, diabetes mellitus includes both type 1 diabetes mellitus and type 2 diabetes mellitus.

As used herein, the term "obesity" is a state in which adipose tissue is excessively accumulated in the body, and when the body obesity index (body mass index: a value obtained by dividing the body weight (kg) by the square of height (m)) at the time of diagnosis is 25 or more, the state is defined as obesity. The fatty acids and glucose introduced into the adipocytes from plasma are esterified and accumulated typically in the form of neutral fat.

As used herein, the term "prevention" refers to all actions that suppress a diabetic disease or delay the onset of the diabetic disease by administering the composition according to the present invention.

As used herein, the term "treatment" refers to all actions in which symptoms of a metabolic disease are ameliorated or beneficially altered by administering the composition according to the present invention.

As used herein, the term "glucagon like peptide-1 (GLP-1) belongs to the incretin family and is a polypeptide secreted by L cells of the small intestinal mucosa, and there are two active forms which are GLP-1-(7-37) and GLP-1-(7-36)-amide. GLP-1 exhibits an antidiabetic effect by binding to a specific receptor glucagon-like peptide 1 receptor (GLP1R), and it is known to control body weight by increasing satiety and reducing appetite by main physiological functions such as improving pancreatic β-cell functions, promoting insulin secretion, maintaining a normal blood sugar state by lowering postprandial blood sugar, enhancing insulin biosynthesis, suppressing glucagon secretion, suppressing gastric peristalsis, particularly gastric emptying.

The GLP-1 may include a base sequence of SEQ ID NO: 5, and in this case, the GLP-1 may include a base sequence having a sequence homology of 70% or more, preferably 80% or more, more preferably 90% or more, even more preferably 95% or more, and most preferably 98% or more with the base sequence represented by SEQ ID NO: 5, respectively.

The oral composition according to the present invention includes the gene carrier and the GLP-1 gene as active ingredients, and may further include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the oral composition according to the present invention may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in Remington's literature. The pharmaceutical composition of the present invention is not particularly limited in formulation, but may be formulated into an injection, an inhalant, an external preparation for skin, or the like.

The composition of the present invention may be orally administered or may be parenterally administered (for example, applied intravenously, subcutaneously, intraperitoneally, or locally), but may be preferably orally administered, and the administration dose may vary depending on a patient's condition and body weight, severity of disease, drug form, and administration route and period according to the target method, but the administration dose may be properly selected by those skilled in the art.

The composition of the present invention is administered in a pharmaceutically effective amount. As used herein, the "pharmaceutically effective amount" refers to an amount sufficient to treat or diagnose diseases at a reasonable benefit/risk ratio applicable to medical treatment or diagnosis, and an effective dosage level may be determined according to factors including the type of disease of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, an effective amount of the pharmaceutical composition of the present invention may vary depending on the age, sex, condition, and body weight of a patient, the absorption of the active ingredients in the body, inert rate and excretion rate, disease type, and the drugs used in combination, and in general, 0.001 to 150 mg, preferably 0.001 to 100 mg of the pharmaceutical composition of the present invention per 1 kg of a body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present invention in any way.

As yet another aspect of the present invention, the present invention provides a method for treating metabolic diseases, the method including: administering the oral composition to an individual.

As used herein, the "individual" refers to a subject in need of treatment of a disease, and more specifically, refers to a mammal such as a human or a non-human primate, a mouse, a rat, a dog, a cat, a horse, and a cow.

Further, the present invention provides a use of the composition for preventing or treating metabolic diseases.

Hereinafter, preferred examples for helping the understanding of the present invention will be suggested. However, the following examples are provided only to more easily understand the present invention, and the contents of the present invention are not limited by the following examples.

EXAMPLES

Example 1. Experimental Preparation and Experimental Methods 1-1. Preparation of Experimental Materials Fluorescein isothiocyanate (FITC) and Bobo-3 Iodide (570/602) chemically coupled dyes were ordered from Thermo Fisher Scientific and used, and organic solvents were purchased from various suppliers.

Further, Lipofectamine™ plus was purchased from Thermo Fisher Scientific, Exfection™ LE mini was purchased from GeneAll Biotechnology (Korea), cell culture media Minimum Essential medium (MEM), RPMI 1640, and Dulbecco's Modified Eagles Medium (DMEM), Dulbecco's Phosphate Buffered Saline (PBS), and trypsin were purchased from Sigma Aldrich (Taufkirchen, Germany) and used, and fetal bovine serum (FBS) was purchased from EMD Millipore Corp. (USA) and used. As cell culture plastics and other disposable plastics, products produced by SPL Life Science (Korea) were used.

Furthermore, human epithelial colon adenocarcinoma cell lines (Caco-2 and HT-29), a human embryonic kidney cell line (HEK-293), and a human cervical cancer cell line (HeLa) were purchased from Korean Cell Line Bank (KCLB, Korea) and used, a GLP-1 ELISA kit was purchased from Sigma-Aldrich (USA), and as a pAcGFP-N1 expression vector, the pAcGFP-N1 expression vector provided by Konkuk University (Chungju, Korea) was used. Finally, a pβ-sp-GLP-1 expression vector was provided by Hanyang University (Seoul, Korea).

1-2. Construction of hIgG1-Fc-9Arg Expression Vector

An expression vector for an Fc region of Human IgG1 was provided by Korea Research Institute of Bioscience and Biotechnology (KRIBB), and a 9-arginine tail was engineered at the C-terminus of the peptide to facilitate purification.

In this case, the sequence of a renal peptide including amino acids is as follows:

RRRRRRRRRGGGSRRRRRRRRR (9 Arg-GGGS-9 Arg)

The sequence is located downstream of hIgG1-Fc and has a 9-Arg chain at the C-terminus.

1-3. Expression and Purification of hIgG1-Fc-9Arg in HEK293F Cells

In order to isolate a recombinant protein from a culture supernatant, a supernatant of an HEK293F cell culture infected with the ExpiFectamine™ 293 transformation reagent (Thermo Fisher Scientific) was collected by 0.22 μm microfiltration. Thereafter, a final product was obtained through a Protein A-HiTrap Mabselect SuRe column (GE Lifesciences, Buckinghamshire, England) treatment according to the protocol provided for purifying antibodies from the culture supernatant of transformed HEK293F cells.

1-4. Preparation of hIgG1-Fc-9Arg/pDNA Complex

The formation of a complex between higG1-Fc-9Arg and pDNA was analyzed using 1% agarose gel electrophoresis. In this case, the complex was prepared as shown in the following Table 1, and prepared by mixing 1 μl of an aqueous pDNA solution (1 mg/1 ml in TE buffer) with 1 μl of hIgG1-Fc-9Arg (9 μg/1 mL in PBS) and 18 μl of PBS (pH 7.4) in a micro-centrifuge tube.

TABLE 1

| | hIgG1-Fc-9Arg/pAcGFP-N1 (weight ratio) | | | | | |
|---|---|---|---|---|---|---|
| | 5/1 | 20/1 | 50/1 | 80/1 | 100/1 | 200/1 |
| pDNA (ul) | 5 | 5 | 5 | 5 | 5 | 5 |
| hIgG1-Fc-9Arg (ul) | 1.10 | 4.30 | 10.80 | 17.30 | 21.60 | 43.20 |
| PBS (ul) | 198.90 | 195.70 | 189.20 | 182.70 | 173.40 | 151.80 |
| Total volume | | | 200 ul (9 ng/ul) | | | |

Next, hIgG1-Fc-9Arg/pDNA complex products were allowed to stand at room temperature for 30 minutes to accelerate complexation, and were reacted at 100 V in the presence of ethidium bromide (0.1 μg/mL) and a tris-acetate-EDTA (TAE) buffer on a 1% agarose gel for 30 minutes to analyze whether a final complex was produced.

1-5. Atomic Force Microscope and Transmission Electron Microscope

In order to confirm the formation of the complex prepared by the method in Example 1-4, AFM (Multimode-N3-AM, Bruker, Germany) and FE-EM (Field Emission Electron Microscope, JEM-2100F, JEOL) were used.

More specifically, the AFM volume of hIgG1-Fc-9Arg and an hIgG1-Fc-9Arg/pDNA complex was measured using Gwyddion software, and then an hIgG1-Fc-9Arg/pDNA complex was imaged using FE-EM, and the form and size after binding were confirmed. In this case, as a pretreatment process, nanoparticles were spread on a silicon wafer substrate and then stained with 2% uranyl acetate, and observation was performed under high vacuum mode and 20 kV conditions.

1-6. Confirmation of Stability of Complex Against pH and Serum

The hIgG1-Fc-9Arg/pDNA complex was evaluated by treating the culture medium 3-fold after the formation of the complex. More specifically, hIgG1-Fc-9Arg/pDNA nanoparticles were diluted with a fetal bovine serum (FBS) protein and cultured at 37° C., and stability over time was confirmed. After EDTA was added to the complex according to the corresponding analysis time, 1% agarose gel electrophoresis was performed.

1-7. Cell Uptake and Endosome Escape Study

In order to confirm hIgG1-Fc-9Arg uptake in cells, a confocal microscope was used, and in this case, hIgG1-Fc-9Arg was labeled with fluorescein (FITC) and used in order to observe the delivery of the hIgG1-Fc-9Arg/pDNA complex to an FcRn target.

More specifically, after cells were aliquoted into a 24-well plate and cultured for 3 days, the culture medium was exchanged with FBS-free MEM medium 1 hour before complex treatment, and then cells were treated with 10 μg of FITC-labeled-hIgG1-Fc-9Arg, and then cultured.

Next, the cells were washed three times with PBS at each analysis time, fixed with 4% paraformaldehyde (PFA), and treated with LysoTracker for 10 minutes for an endosomal trafficking study to stain late endosomes and lysosomes, and images were observed with a confocal laser scanning microscope.

1-8. Confirmation of Delivery of Complex by Caco-2 Intracellular Permeation

In order to determine endosomal trafficking of the hgG1-Fc-9Arg/pDNA complex via FcRn, a monolayer Transwell permeability assay was performed using Caco-2 cells.

More specifically, first, a monolayer membrane was formed by culturing cells in a Transwell plate (a cell culture insert with a pore size of 0.4 μm and a diameter of 12 mm, Millipore), and then the cell layer was serum-starved, and a bobo-3-labeled-pDNA-encapsulated complex applied to the apical side from 1 μg of pDNA (HBSS, pH 6.0) was put into the serum. The apical-basolateral translocation thereof was determined by measuring the presence of hIgG1-Fc-9Arg or bobo-3-labeled-pDNA in a basolateral medium (HBSS, pH 7.4) at 10, 30, and 60 minutes and 2, 4, 10, 12, and 24 hours. Thereafter, the bobo-3-labeled-pDNA was quantified by microplate spectrometry using a 96-well plate, the cells were fixed with 4% paraformaldehyde, and then images were taken.

1-9. Transfection Experiment of hIgG1-Fc-9Arg/pAcGFP-N1

After Caco-2 cells were cultured along with hIgG1-Fc-9Arg/pAcGFP-N1 in an FBS-containing culture with a pH of 6.0 at 37° C. for 1, 2, 5, 10, and 21 days, the plate was washed three times with PBS and fixed with 4% paraformaldehyde for 5 to 10 minutes, and all results were observed with a confocal laser scanning microscope.

1-10. Plasmid DNA Transfection Using Lipofectamine

A Lipofectamine™ plus (LF) complex was prepared according to the manufacturer's protocol. More specifically, DNA was diluted with 75 μl of Opti-MEM, and the PLUS reagent was added thereto at a concentration of 1.2 μl per μg of DNA. Thereafter, LF was diluted with 75 μl of Opti-MEM, and then cultured for 5 minutes, and an LF solution was added to a mixture containing the DNA and the PLUS reagent. After being cultured for 5 minutes, the complex was added to the cells.

1-11. Animal Model Preparation

In order to perform an animal experiment, Balb/c mice (5 to 7 week old) and db/db mice (male, 7 to 9 week old) were purchased from Daehan Bio Link, Inc. (Chungcheongbukdo, Korea), and for all the purchased mice, 3 mice per cage in sterilized autocages were maintained with a standard diet. In this case, all animal experiments followed the guidelines established by the animal laboratory utilization committee of Chonnam National University, and appropriate approval was obtained before the study.

1-12. Confirmation of Binding Affinity of hIGg1-Fc-9Arg to Mouse FcRn in Balb/c Mouse Model Organs The mice prepared from Example 1-11 were orally administered 10 μg of FITC-hIgG1-Fc-9Arg, and sacrificed after 1 hour and 3 hours. The mouse organs were washed three times with PBS and then collected, and fluorescence images were taken with a Kodak Digital Science™ Image Station 440CF (IS440CF) system. The fluorescence intensity in each organ was measured by microplate spectrometry.

Example 2. Confirmation of Recombination of Antibody hIgG1-Fc-9Arg

In order to form the complex according to the present invention, gene recombination was performed using a base sequence of an Fc region which is a constant region of an antibody IgG.

Figure 1B:
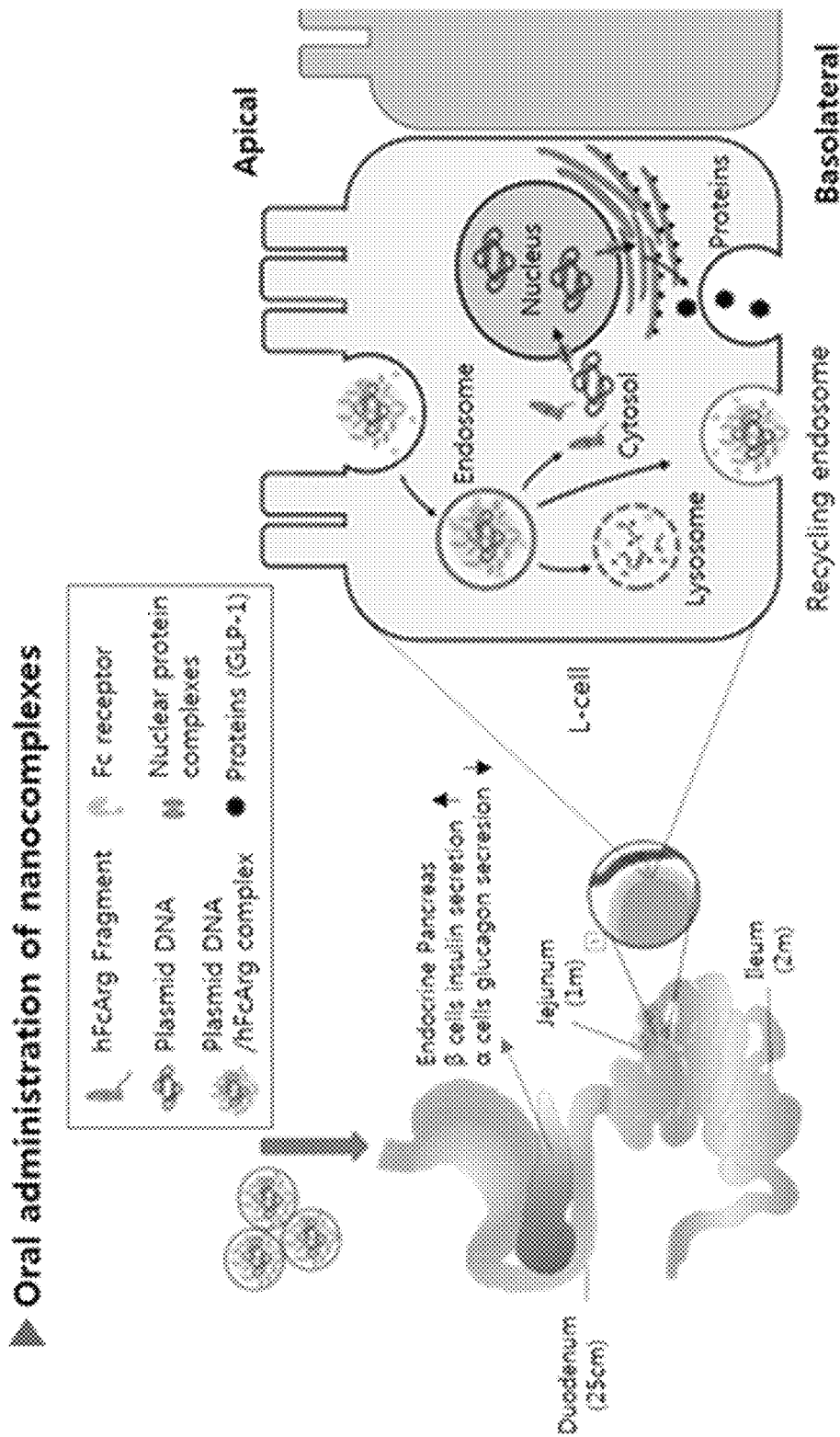
FIG. 1B shows a process by which an antibody-therapeutic gene complex is delivered in the body through cell receptors.

More specifically, as illustrated in FIG. 1A, since it is difficult to effectively condense a gene having anionic properties using only an Fc portion of the antibody due to phosphoric acid groups, cloning was performed by binding nine arginines which are amino acids having cationic properties to the C-terminus of the Fc region to insert the nine arginines into an expression vector in order to overcome this difficulty, and antibodies were produced by transfecting an HEK 293F cell line with the expression vector. As a result of the experiment, the recombined complex forms an Fc-based receptor having low immunogenicity, as illustrated in FIG. 1B, so that it is expected to be able to effectively deliver a drug by oral administration.

Figure 2:
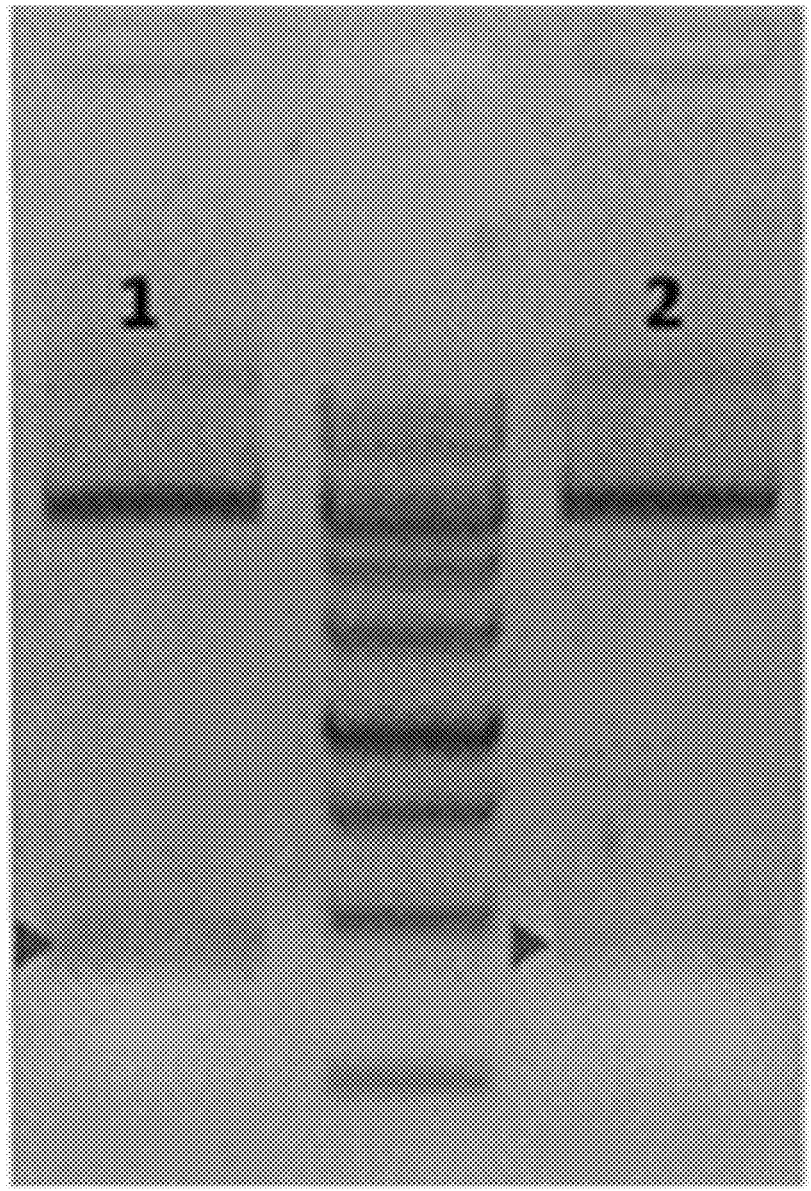
FIG. 2 shows the results of SDS-PAGE of an antibody in which nine arginines are bound to a Human IgG1-Fc portion ((850 bp), Lane 1.pcr annealing TM=55° C., Lane 2.pcr annealing TM=52° C.).

Further, in the case of hIgG1-Fc-9Arg, the extension size was long, so that in order to confirm the binding efficiency of a primer, a reaction product was confirmed by electrophoresis after the PCR was performed by changing the annealing temperature. As a result, as illustrated in FIG. 2, when the No. 1 annealing temperature was 55° C. and the No. 2 annealing temperature was 52° C., the annealing of hIgG1-Fc-9Arg was performed normally under both temperature conditions, so that it was confirmed that it was expressed with a size of 850 bp. That is, it could be confirmed that the change in temperature from 52° C. to 55° C. did not affect the progress of PCR.

Figure 3:
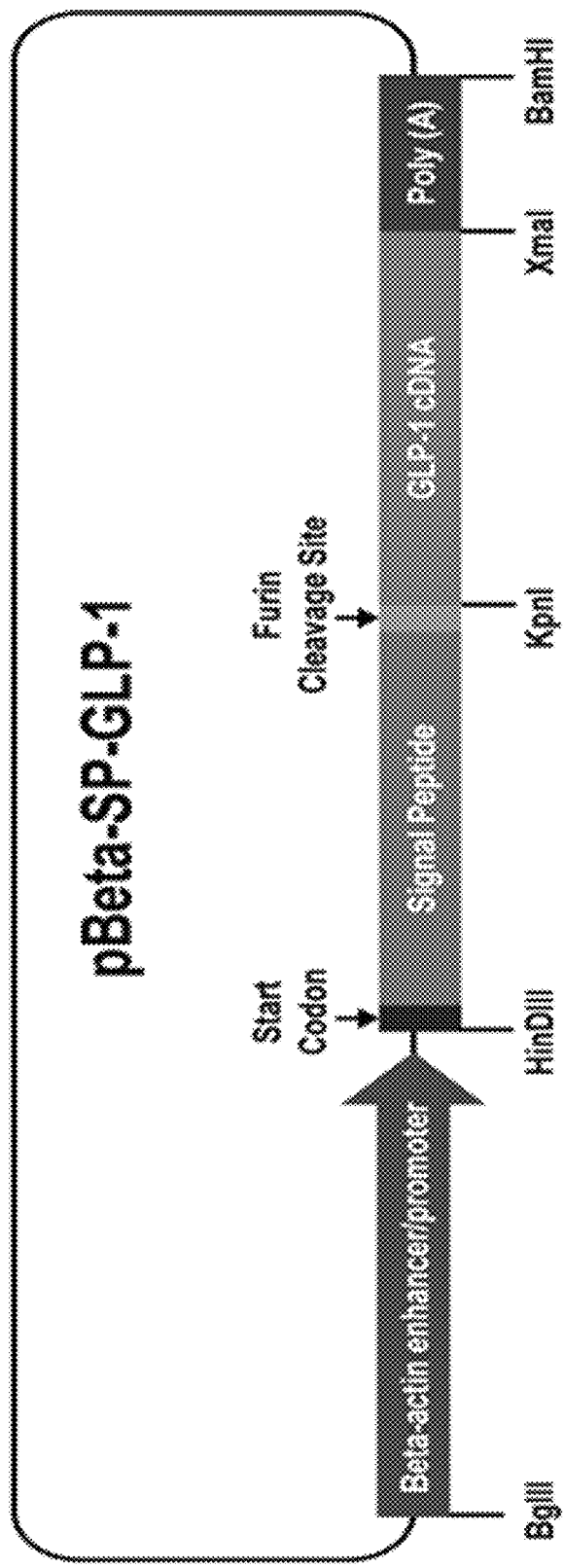
FIG. 3 shows a result confirming that a gene was normally cloned by extracting recombinant hIgG1-Fc-9Arg to perform a gene sequencing analysis through the presence of a Kozak nucleotide sequence at the 5 terminus and a start codon.

In addition, in order to confirm whether the recombinant gene was cloned normally, gene sequencing analysis was performed by performing treatment with restriction enzymes to extract the recombinant hIgG1-Fc-9Arg. As a result, as illustrated in FIG. 3, a Kozak nucleotide sequence at the 5 terminus and the start codon were confirmed, confirming that the cloning was performed normally.

Figure 4:
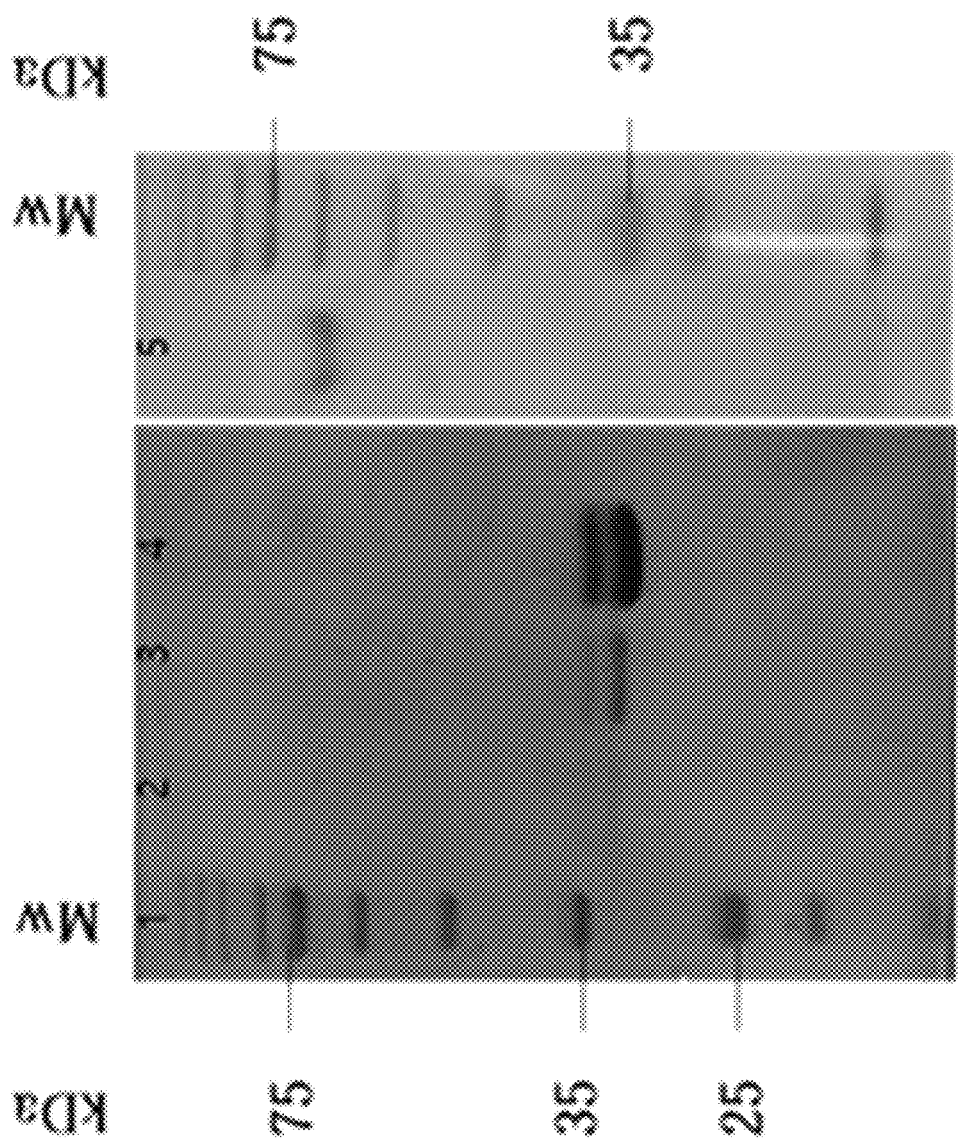
FIG. 4 shows an SDS-PAGE result for confirming the molecular weight of purified antibody hIgG1-Fc-9Arg (used (Protein Ladder 10-245 kDa). Lane 2: 0.1 µg, Lane 3: 1 µg, Lane 4: 10 µg antibodies) and a molecular weight result of hIgG1-Fc-9Arg which maintains S—S bonding under the non-reduction conditions (Lane 5).

Furthermore, as a result of expressing and purifying hIgG1-Fc-9Arg and confirming the hIgG1-Fc-9Arg through SDS-PAGE, as illustrated in FIG. 4, it was confirmed that the size of hIgG1-Fc-9Arg was 30 to 35 kDa, the reason that bands appeared in two rows is because the Fc portion of the antibody includes two heavy chains, and it was confirmed that hIgG1-Fc-9Arg had a size of 70 kDa under non-reducing conditions in which S—S bonds were formed.

Example 3. Identification of Characteristics of hIgG1-Fc-9Arg/pDNAcomplex 3-1. Confirmation of Functionality as Gene Carrier In order to confirm whether the hIgG1-Fc-9Arg could be used as an efficient gene carrier, agarose gel electrophoresis, AFM, and TEM image analyses were performed.

Figure 5:
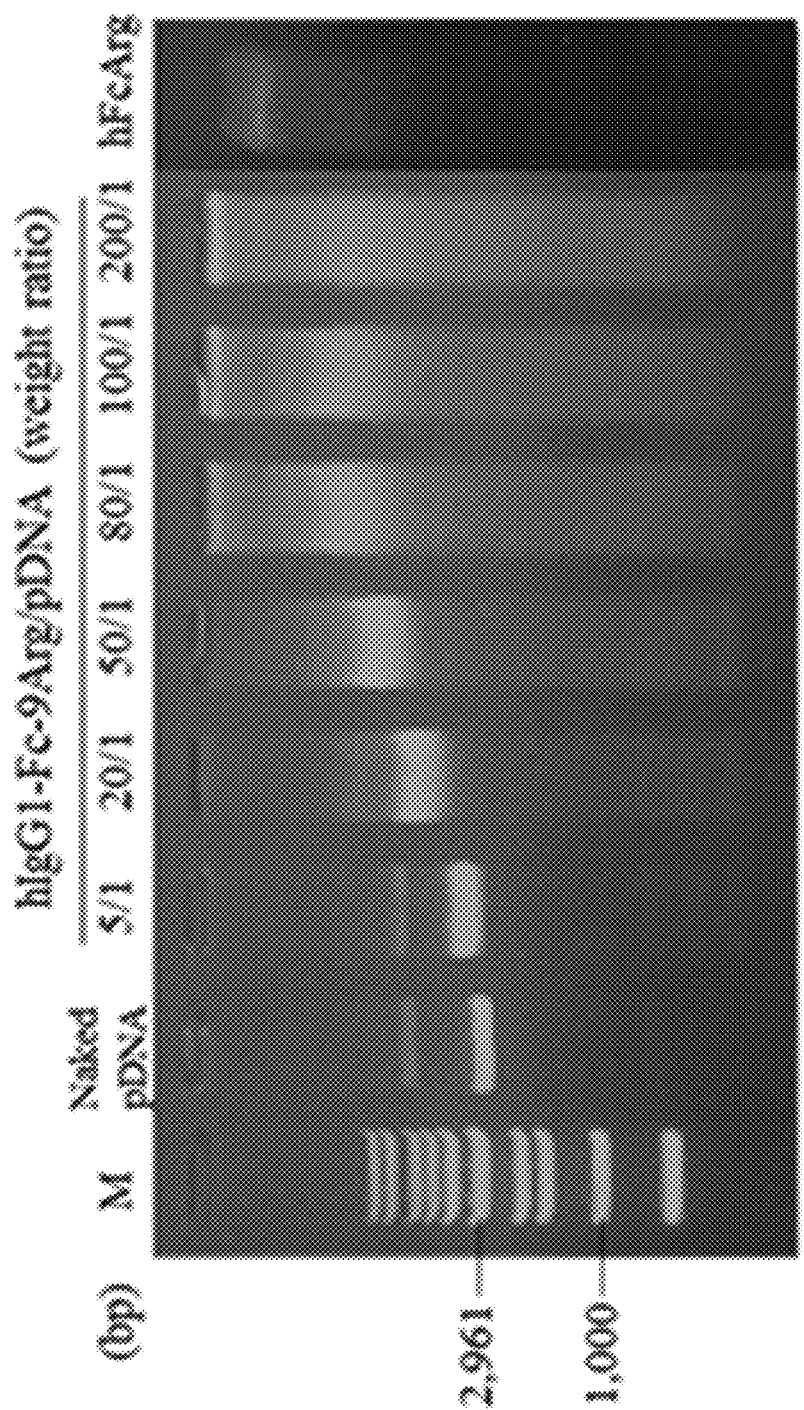
FIG. 5 shows an agarose gel electrophoresis result for a complex of hIgG1-Fc-9Arg and pDNA (0.8% agarose gel).

More specifically, after the complex formation of hIgG1-Fc-9Arg and plasmid DNA was induced by maintaining the amount of pDNA equal and making each mass ratio of hIgG1-Fc-9Arg different, the formation of the complex was confirmed by 0.8% agarose gel electrophoresis. As a result, as illustrated in FIG. 5, it was confirmed that the complex was formed starting from a ratio of 20/1.

Figure 6:
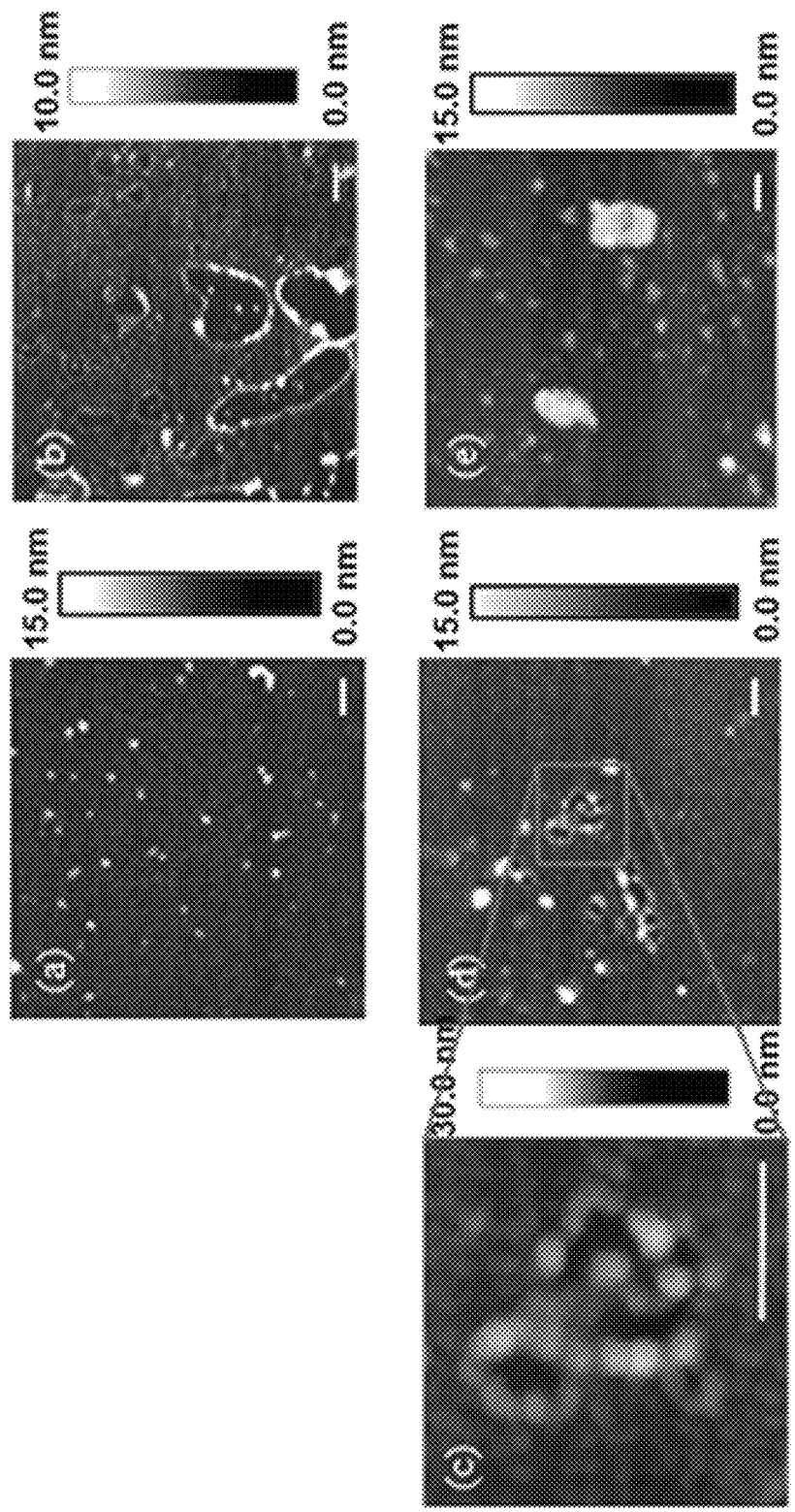
FIG. 6 shows TN-AFM imaging results of hgG1-Fc-9Arg/pDNA complexes, and shows imaging results of (A) hIgG1-Fc-9Arg, (B) an hIgG1-Fc-9Arg/pDNA complex at a 20/1 ratio (w/w), (C and D) an hIgG1-Fc-9Arg/pDNA complex at a 50/1 ratio (w/w), and (E) an hIgG1-Fc-9Arg/pDNA complex at a 100/1 ratio (w/w)(Scale bars 200 nm).

Further, as a result of TM-AFM imaging in FIG. 6, the structure of DNA was confirmed because the ratio of 20/1 failed to form a perfect complex, but it was confirmed that at the ratio of 50/1 and 100/1, hIgG1-Fc-9Arg and plasmid DNA formed a complete complex to form a spherical shape.

Figure 7:
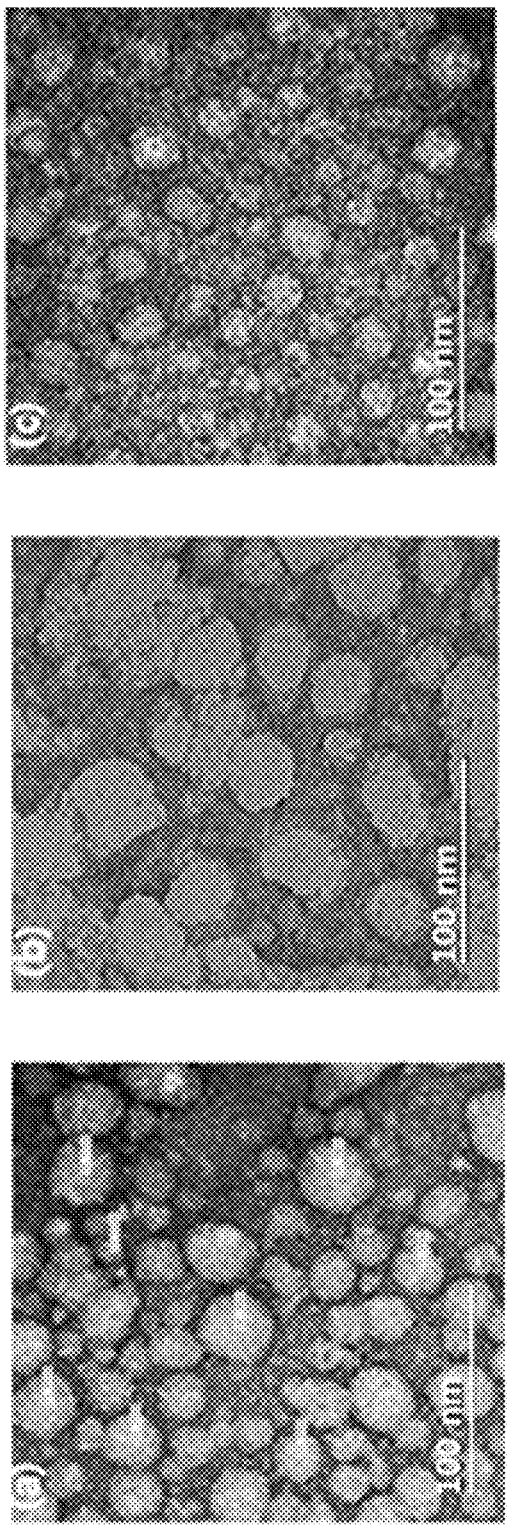
FIG. 7 shows TEM imaging results of hIgG1-Fc-9Arg/pDNA complexes, and shows imaging results of (A) an hgG1-Fc-9Arg/pDNA complex at a 20/1 ratio (w/w), (B) an hIgG1-Fc-9Arg/pDNAcomplex at a 50/1 ratio (w/w), and (C) an hIgG1-Fc-9Arg/pDNA complex at a 100/1 ratio (w/w)(Scale bars 100 nm).

In addition, as shown in FIG. 7 and the following Table 2, as a result of confirming the formation of the complex and the size of the complex by TEM images, it was confirmed that complexes having an average diameter size of 100 nm or less were uniformly formed, and it was confirmed that at a ratio of 100/1, cationic properties were increased due to the increased hIgG1-Fc-9Arg mass ratio to condense the plasmid to a smaller size than the other mass ratios. Through this, it was confirmed that at the ratio of 50/1 or more, a perfect complex was formed.

TABLE 2

| Ratio (w/w) | Mean size ± SD (nm) |
| --- | --- |
| 20/1 | 25.71 ± 7.40 |
| 50/1 | 43.31 ± 17.98 |
| 100/1 | 19.23 ± 4.80 |

3-2. Confirmation of Acid Stability of Gene Carrier

In order to confirm the possibility of oral administration, stability against gastric acid and systemic enzymes was verified. More specifically, first, hIgG1-Fc-9Arg was reacted for 0 minute, 30 minutes, and up to 60 minutes, respectively under various pH conditions (pH 1.5, 5.0, 6.0, and 7.4), and then it was confirmed whether hgG1-Fc-9Arg was stable through SDS-PAGE.

Figure 8:
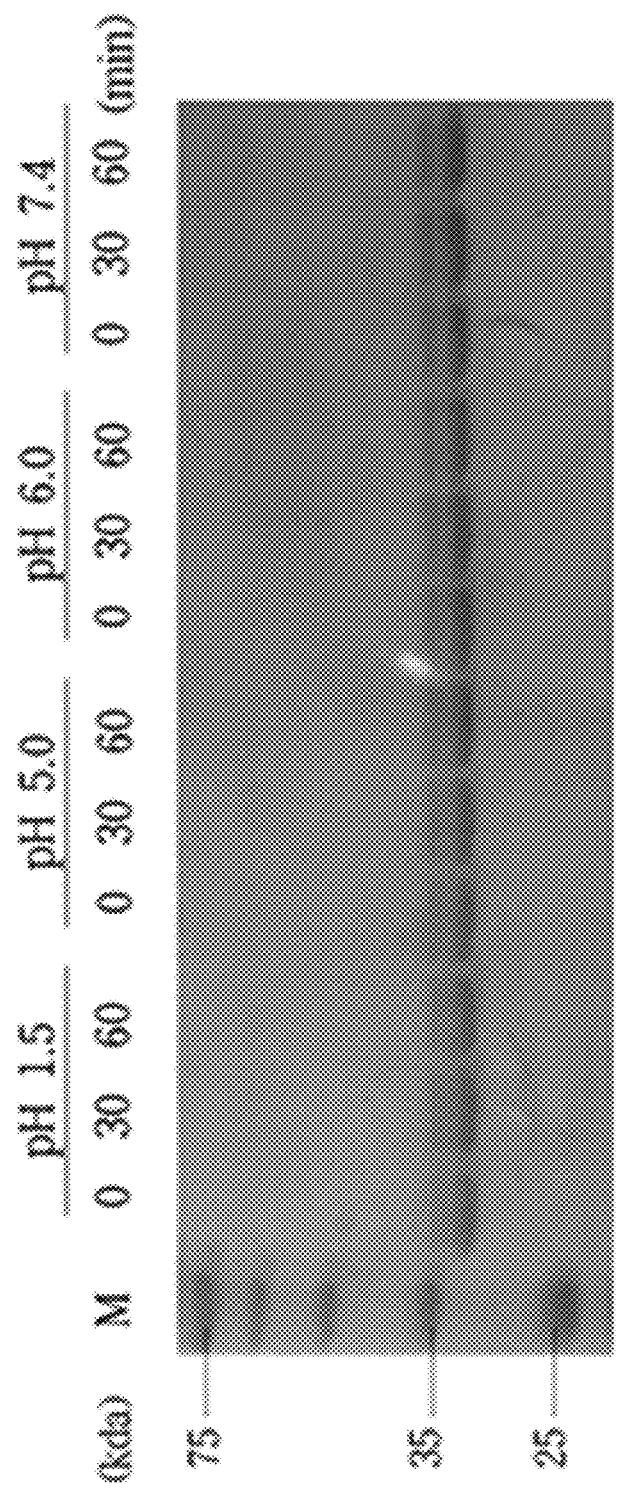
FIG. 8 shows the results of SDS-PAGE confirming the stability of antibody hIgG1-Fc-9Arg overtime under various pH conditions (pH 1.5, 5.0, 6.0, and 7.4).
Figure 9:
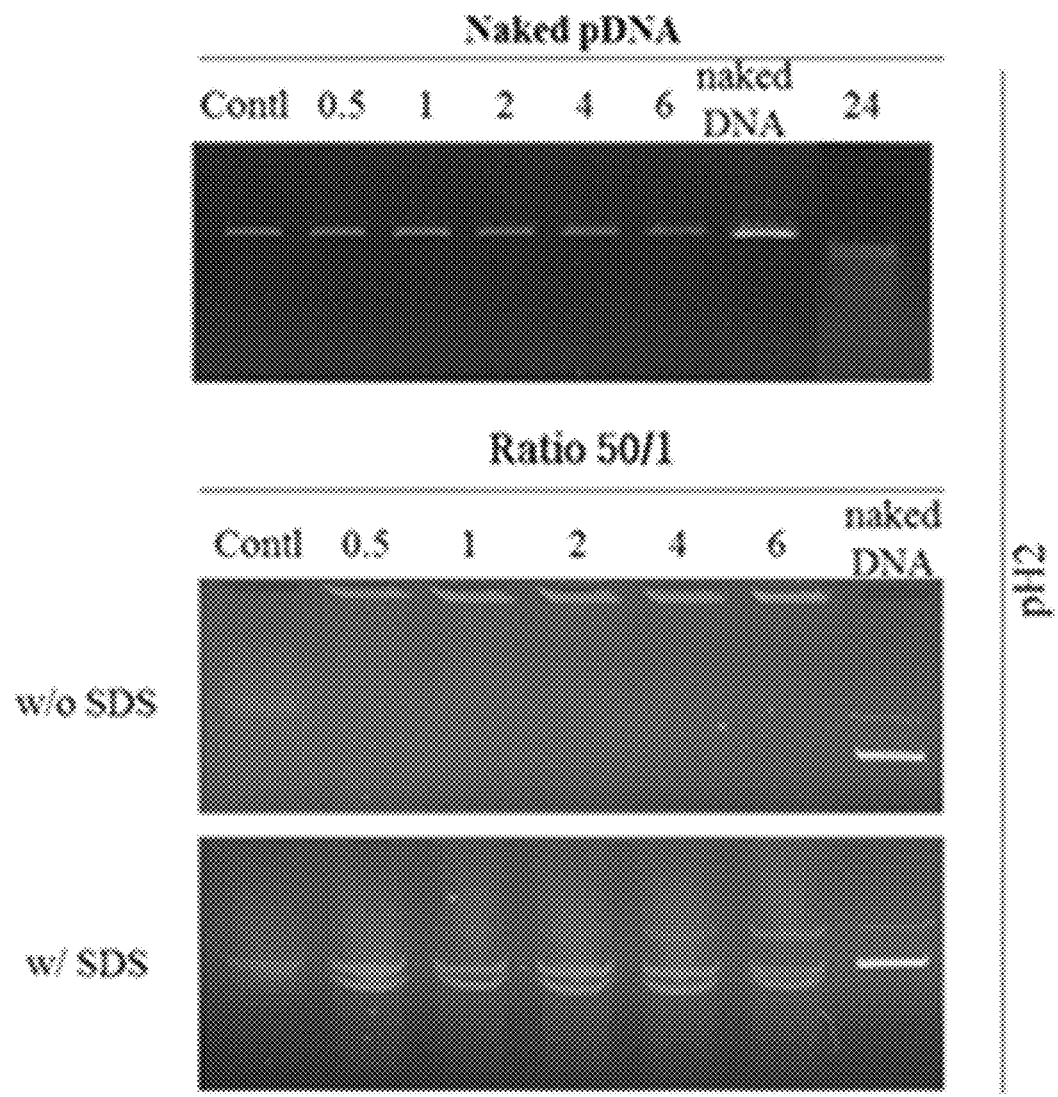
FIG. 9 shows the results of agarose gel (0.8%) electrophoresis confirming the stability of plasmid DNA and an hIgG1-Fc-9Arg/pDNA complex at pH 2.0 under gastric acid conditions.

As a result, as illustrated in FIGS. 8 and 9, it was confirmed by electrophoresis that hIgG1-Fc-9Arg maintained stability at a pH of 1.5 which is a condition similar to that of gastric acid for 60 minutes to exhibit a size of 30 to 35 kDa in an SDS-PAGE gel, maintained stability at a pH interval of 5.0 to 7.4 until 1 hour, and maintained stability at a pH of 2.0 until 30 minutes. Further, it was confirmed that using plasmid DNA alone, stability was maintained until 6 hours under strong acid conditions. Through this, it was confirmed that under strong acid conditions, the complex exhibited slight instability, but prevented plasmid DNA from being degraded.

3-3. Confirmation of Enzyme Stability of Gene Carrier

In order to confirm the enzyme stability of the gene carrier, it was confirmed at the cellular level whether the gene carrier was stable against a serum protein (10% fetal bovine serum) present in blood.

More specifically, after naked DNA and complexes at a ratio of 20/1, 50/1, and 100/1 were reacted with the serum protein for time periods of 0 minute, 30 minutes, 2 hours, 4 hours, 7 hours, 10 hours, 12 hours, and 24 hours, stability was confirmed by electrophoresis.

Figure 10:
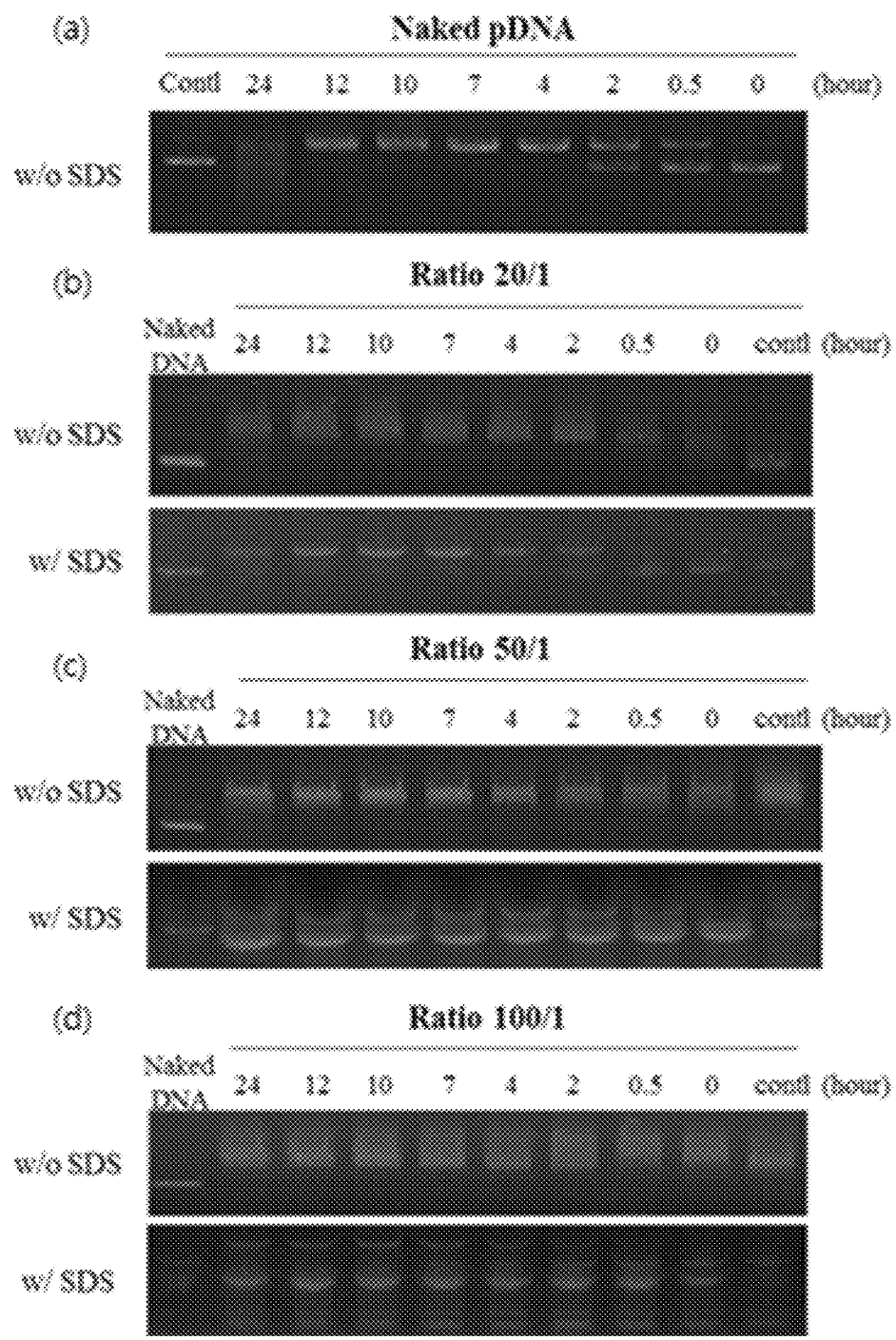
FIG. 10 shows the serum protein stability experiment results of an hIgG1-Fc-9Arg/pDNA complex (10% fetal bovine serum), and shows the stability confirmation results of (a) plasmid DNA, (b) the complex at a 20/1 ratio, (c) the complex at a 50/1 ratio, and (d) the complex at a 100/1 ratio.

As a result, as illustrated in FIG. 10, it was confirmed that the naked DNA began to be degraded after 2 hours and was completely degraded in 24 hours, it was confirmed that genes enclosed in the complexes at a ratio of 20/1, 50/1, and 100/1 were not degraded until 24 hours, and through this, it was confirmed that the stability of the hIgG1-Fc-9Arg/pDNA complex was maintained even in the presence of a serum protein.

Example 4. Measurement of Gene Delivery Efficiency of hIgG1-Fc-9Arg/pDNA Complex in Cells

4-1. Confirmation of Expression of FcRn Receptor in Cells

Before the hIgG1-Fc-9Arg/pDNA complex was delivered into cells, an FcRn receptor in cells was confirmed for various cell lines Caco-2, HT-29, HEK 293, HEK 293-FcRn, and HeLa.

Figure 11:
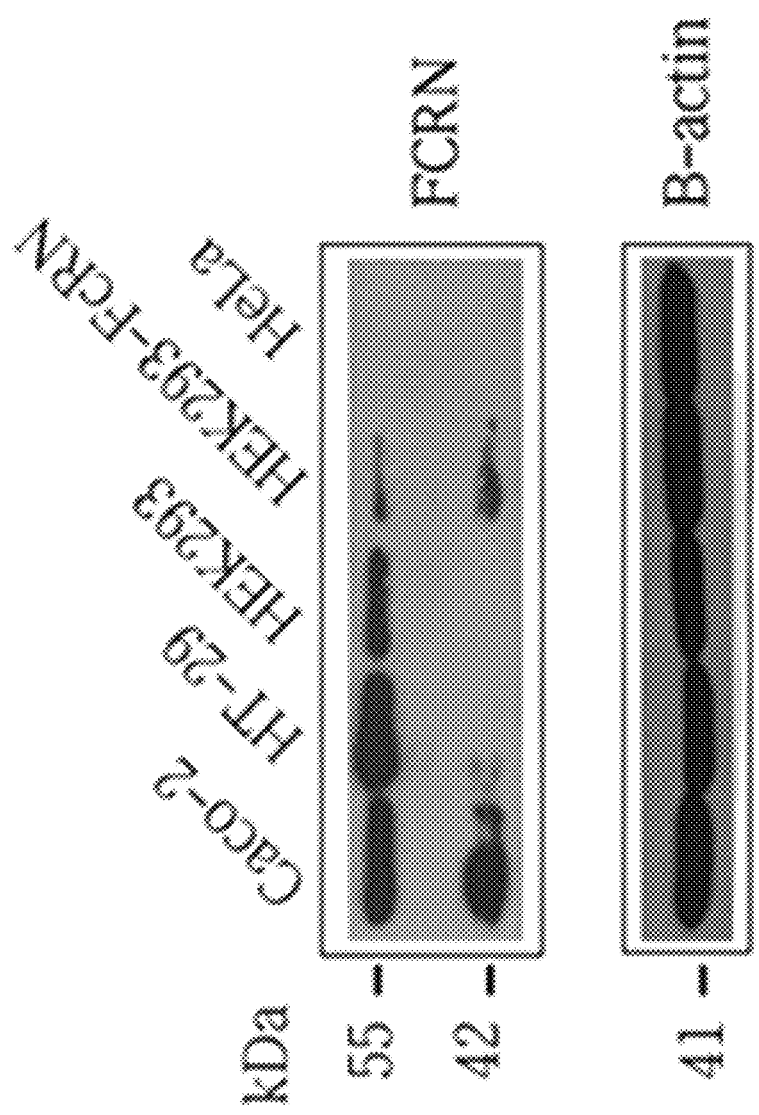
FIG. 11 shows the results of western blotting confirming an FcRn receptor protein present in various cell lines.

As a result, as illustrated in FIG. 11, it was found that the FcRn receptor was not expressed in the HeLa cell line, and it could be confirmed that the expression level of FcRn in the HEK 293-FcRn cell line was shown to be relatively low as compared to those in the Caco-2, HT-29, and HEK 293 cell lines.

4-2. Confirmation of Intracellular Uptake of Antibody hIgG1-Fc-9Arg

This application contains references to amino acid sequences and/or nucleic acid sequences which have been submitted concurrently herewith as the sequence listing text file entitled "000030usnp_SequenceListing.TXT", file size 3 KiloBytes (KB), created on 20 Aug. 2020. The aforementioned sequence listing is hereby incorporated by reference in its entirety pursuant to 37 C.F.R. § 1.52(e)(5).

Figure 12:
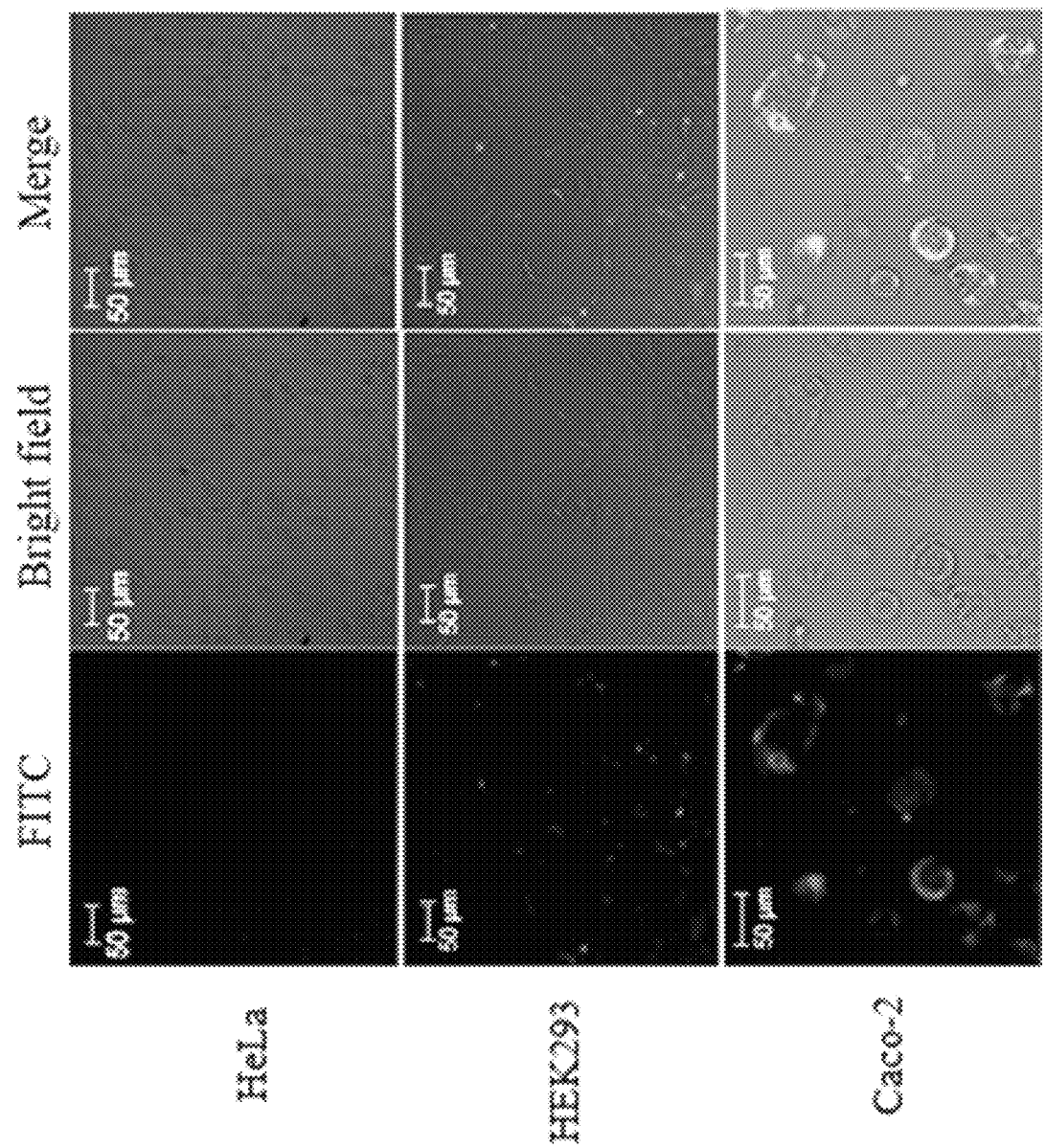
FIG. 12 shows fluorescence imaging results of FITC-hIgG1-Fc-9Arg absorbed by an FcRn receptor (under 1 hour culture condition).

As a result, as illustrated in FIG. 12, it was confirmed that in the case of CaCo-2 and HEK 293 cell lines which are cell lines having the FcRn receptor, green fluorescence appeared because hIgG1-Fc-9Arg were absorbed intracellularly, whereas fluorescence did not appear in the HeLa cell line having no FcRn receptor. Further, through the result, the Caco-2 and HT-29 cell lines were selected as a cell line to be applied to a cell experiment.

Figure 13:
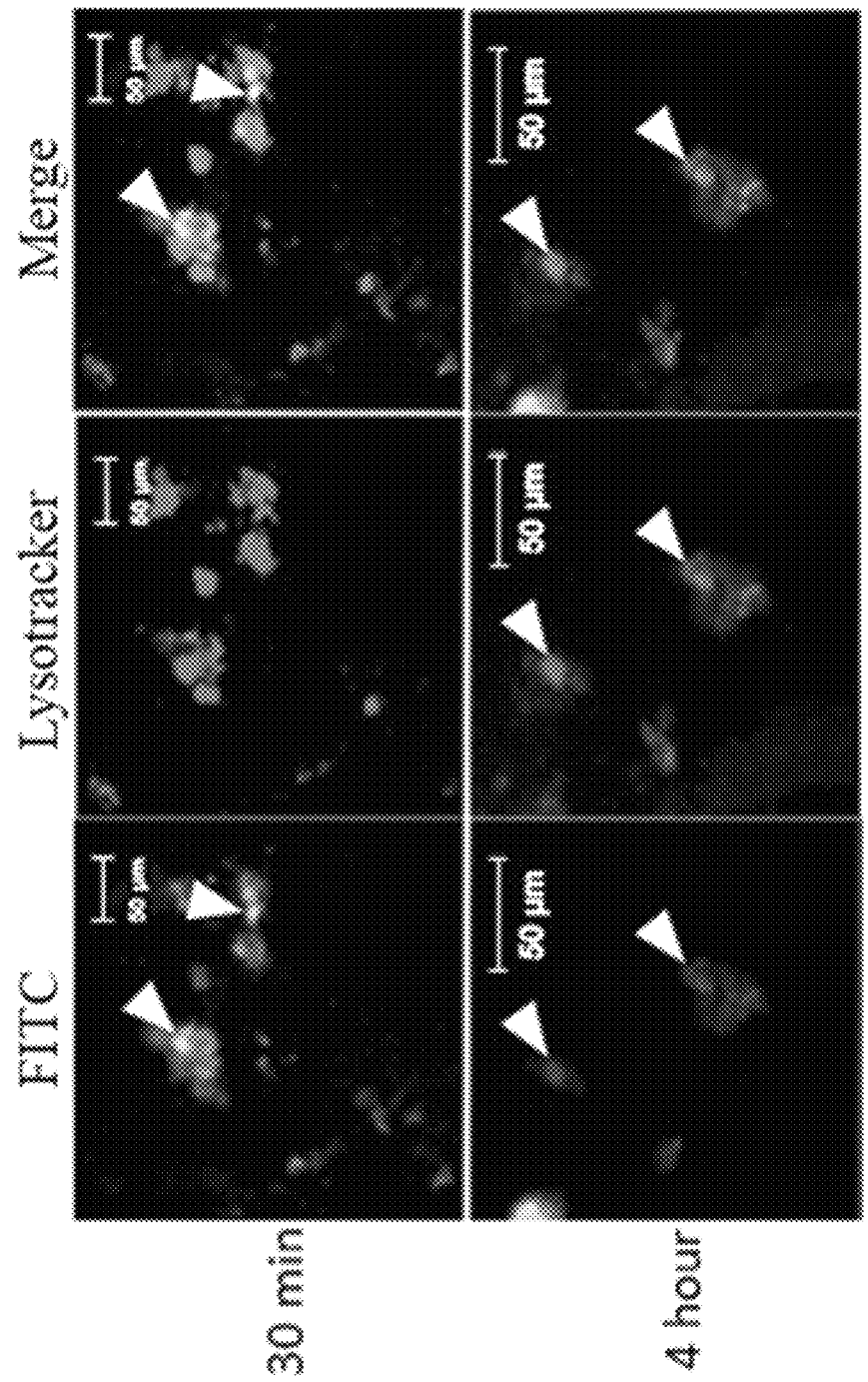
FIG. 13 shows the endosome formation and the endosomal escape fluorescence imaging results of FITC-hIgG1-Fc-9Arg (under reaction conditions of 30 minutes and 4 hours).

In addition, in order to confirm whether the hIgG1-Fc-9Arg/pDNA complex was delivered into cells to form an endosome, the CaCo-2 cell line was treated with FITC-bound antibody hIgG1-Fc-9Arg and allowed to react for 30 minutes and 4 hours, and then stained with Lysotracker, and observed with a confocal microscope. As a result, as illustrated in FIG. 13, through the appearance of green fluorescence in cells, it was confirmed that FITC-hIgG1-Fc-9Arg was delivered into cells, and through overlapping of an FITC-hIgG1-Fc-9Arg green fluorescence image with a red fluorescence image of Lysotracker in a merged image, it was confirmed that the antibody FITC-hgG1-Fc-9Arg was intracellularly delivered to form an endo/lysosome.

4-3. Confirmation of Delivery of hIgG1-Fc-9Arg/pDNA Complex

In order to confirm whether a gene was expressed from the hIgG1-Fc-9Arg/pDNA complex, by binding Bobo-3 (Ex=570 nm, Em=602 nm) to pDNA, it was confirmed whether a gene of the hIgG1-Fc-9Arg/pDNA complex was delivered.

Figure 14:
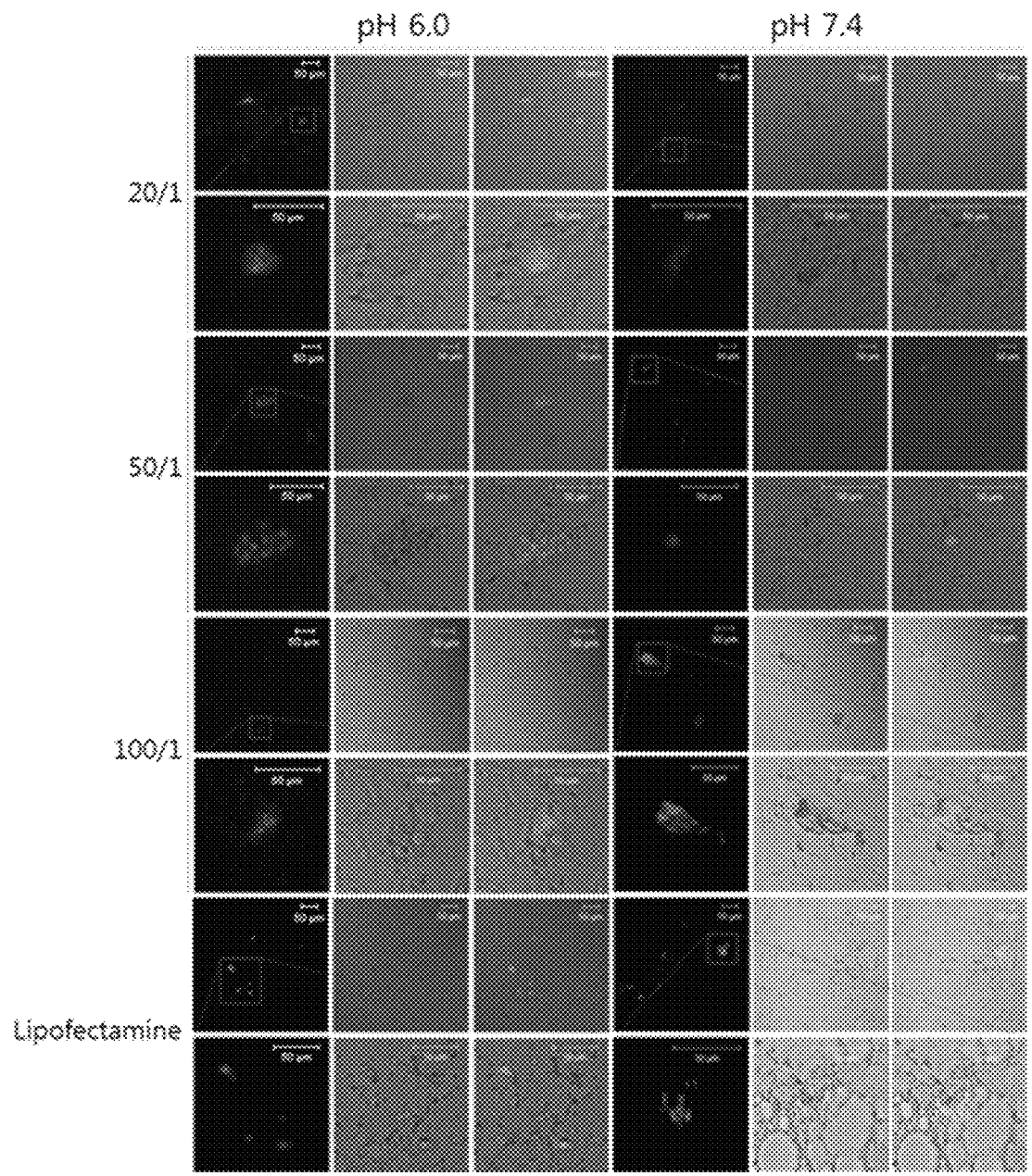
FIG. 14 shows the fluorescence imaging results confirming whether a gene was expressed by treating a Caco-2 cell line with an hIgG1-Fc-9Arg/bobo-3-pDNA complex for 24 hours and treating a control with lipofectamine for 24 hours.

As a result, as illustrated in FIG. 14, as a result of treating the Caco-2 cell line with the complexes at a ratio of 20/1, 50/1, and 100/1 and observing the cell line with a confocal microscope after 24 hours, red fluorescence appeared in the complexes at a ratio of 20/1, 50/1, and 100/1, and in the case of the complex at the ratio of 50/1, the highest fluorescence intensity was observed. Further, since the complex at the ratio of 50/1 exhibited a relatively higher fluorescence intensity than Lipofectamine which was used as a positive control, it was confirmed that an antibody-derived carrier hIgG1-Fc-9Arg developed in the present invention was efficiently delivered into cells.

4-4. Confirmation of Cell Membrane Permeability of Caco-2 Cell Monolayer

As a gene delivery effect can be exhibited only when an orally-administered gene carrier binds with an FcRn receptor of the small intestinal epithelial cell and passes through the epithelial cell membrane, a cell membrane permeability experiment of a Caco-2 cell monolayer was performed.

More specifically, in order to confirm a change in the Caco-2 cell monolayer membrane, the result was confirmed by reacting hIgG1-Fc-9Arg/bobo-3-pDNA complexes at various ratios of 20/1, 50/1, and 100/1 using bobo-3-bound pDNA with the Caco-2 cell monolayer membrane for 24 and 36 hours.

Figure 15:
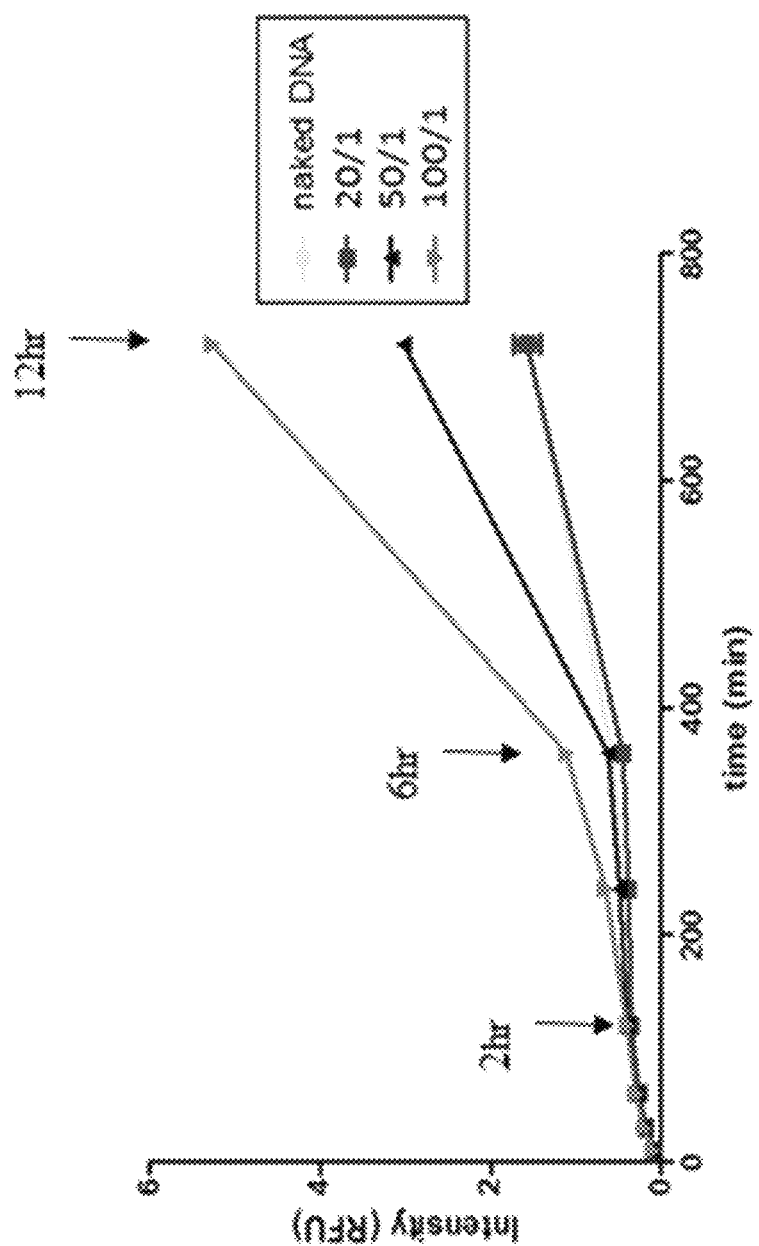
FIG. 15 shows the Caco-2 cell line monolayer membrane permeation experiment results of an hgG1-Fc-9Arg/bobo-3-pDNA complex.

As a result, as illustrated in FIG. 15, it could be confirmed that when the fluorescence intensity of the hIgG1-Fc-9Arg/bobo-3-pDNA complex permeating the inside of the cell membrane was measured, in the case of the ratios of 50/1 and 100/1, the fluorescence intensity was increased from 6 hours, and the fluorescence intensity was relatively high at various complex ratios. Through this, it was confirmed that the complexes at a ratio of 50/1 and 100/1 had relatively high ability to permeate the cell membrane of the Caco-2 cell monolayer.

Figure 16:
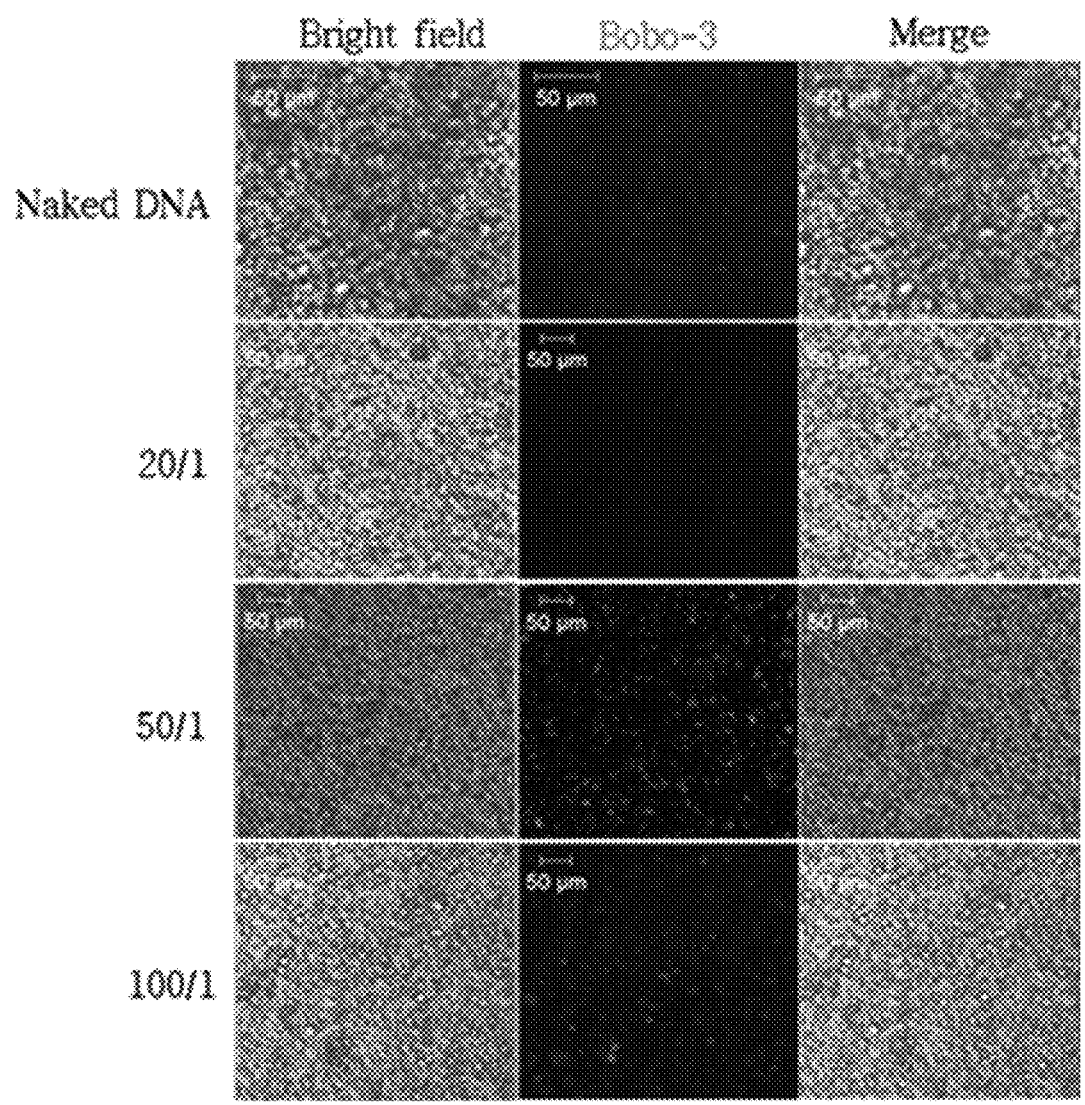
FIG. 16 shows the Caco-2 cell line monolayer membrane permeation fluorescence imaging results of the hgG1-Fc-9Arg/bobo-3-pDNA complex.

Further, as illustrated in FIG. 16, as a result of fluorescence imaging of hIgG1-Fc-9Arg/bobo-3-pDNA absorbed in the Caco-2 cell monolayer, an hgG1-Fc-9Arg/bobo-3-pDNA complex at a ratio of 50/1 showed a higher uptake rate than an hIgG1-Fc-9Arg/bobo-3-pDNA at a ratio of 100/1.

From the foregoing, it was confirmed that the fluorescence intensity was high because the complex at a ratio of 100/1 had a relatively higher permeation rate than an uptake rate of the complex at a ratio of 100/1 binding to the monolayer membrane of Caco-2 cells. In contrast, it could be confirmed that the complex at the ratio of 50/1 showed a high uptake rate in the monolayer membrane of Caco-2 cells and permeability over time was increased. Therefore, it could be inferred that the complex at the ratio of 50/1 could deliver the gene into the small intestine more efficiently than the complexes at other ratios.

Figure 17:
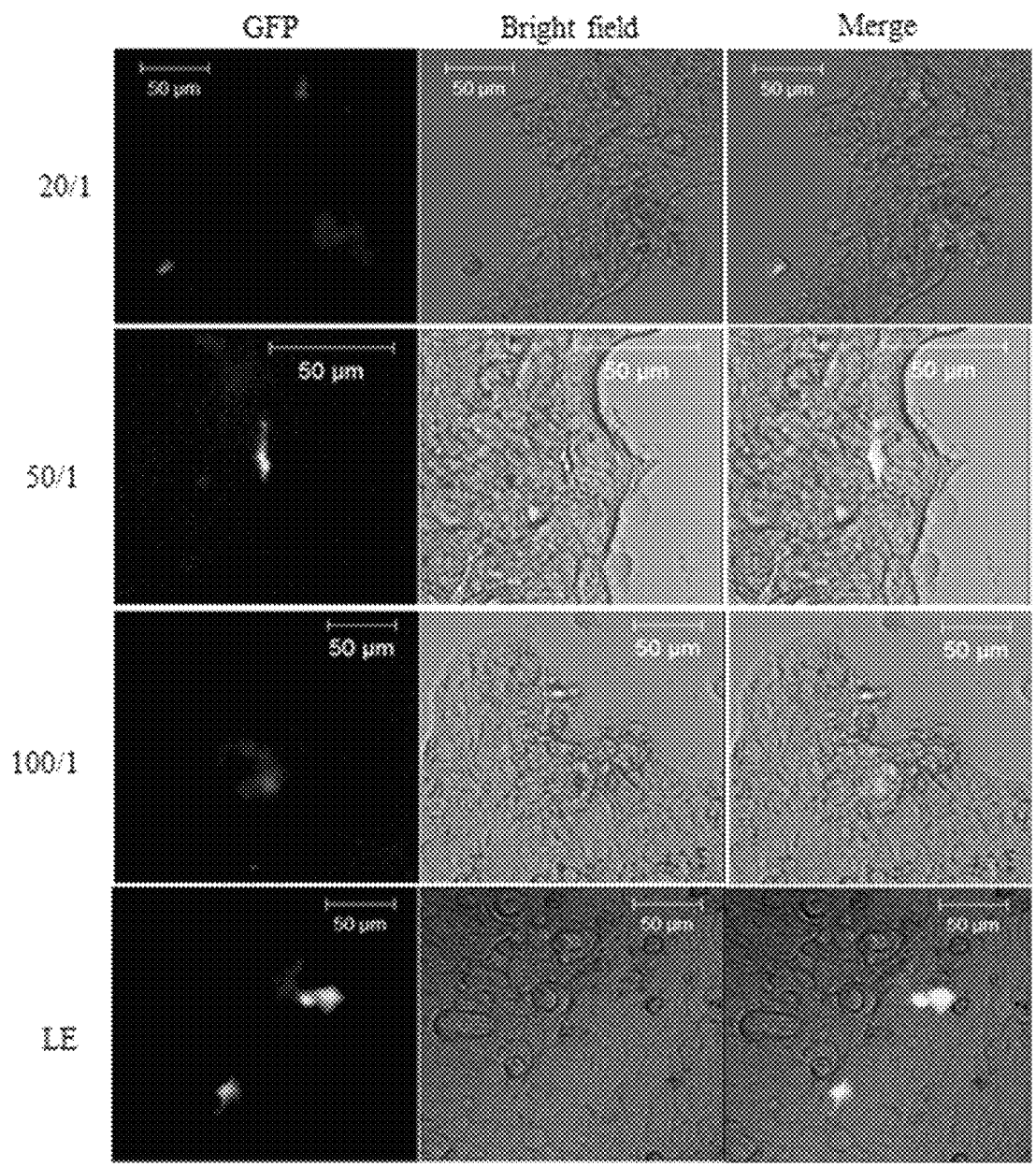
FIG. 17 shows the fluorescence imaging results of pGFP gene expression in Caco-2 cells.

In addition, as a result of confirming whether a gene was expressed by introducing a pGFP gene, as illustrated in FIG. 17, the doubling time of the Caco-2 cell line was 37 hours, so that after cells were treated with the hIgG1-Fc-9Arg/pGFP complex and reacted for 48 hours, as a result of observing the reacted cells with a confocal microscope, it was confirmed that the expression of the pGFP gene proceeded in the complex at the ratio of 50/1, and thus the fluorescence intensity was increased, so that it could be seen that the antibody-derived carrier developed in the present invention efficiently delivered a gene into cells.

4-5. Confirmation of Stability of hIgG1-Fc-9Arg Gene Carrier

The present inventors tried to confirm whether the antibody-derived carrier according to the present invention could be used as a safe carrier.

More specifically, after a Caco-2 cell line was treated with only an hIgG1-Fc-9Arg gene carrier at a concentration of 3.75, 7.5, and 15 μg and reacted for 24 hours, cell viability was measured at an absorbance of 570 nm.

Figure 18A:
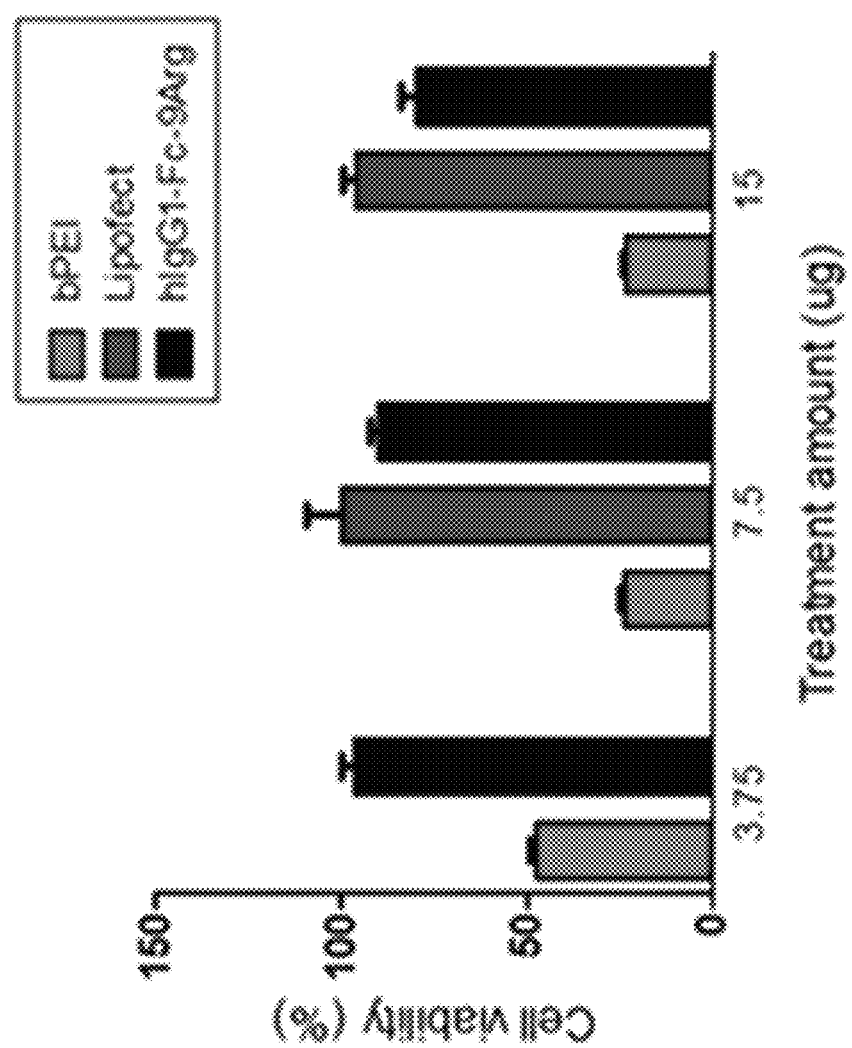
FIG. 18A shows the cytotoxicity experiment results of an hIgG1-Fc-9Arg gene carrier.

As a result, as illustrated in FIG. 18A, it was confirmed that bPEI at a concentration of 15 μg showed a cell viability of 20%, whereas the hIgG1-Fc-9Arg according to the present invention showed a cell viability of 70% or more at the same concentration, and thus was a safe carrier when applied to cells.

Figure 18B:
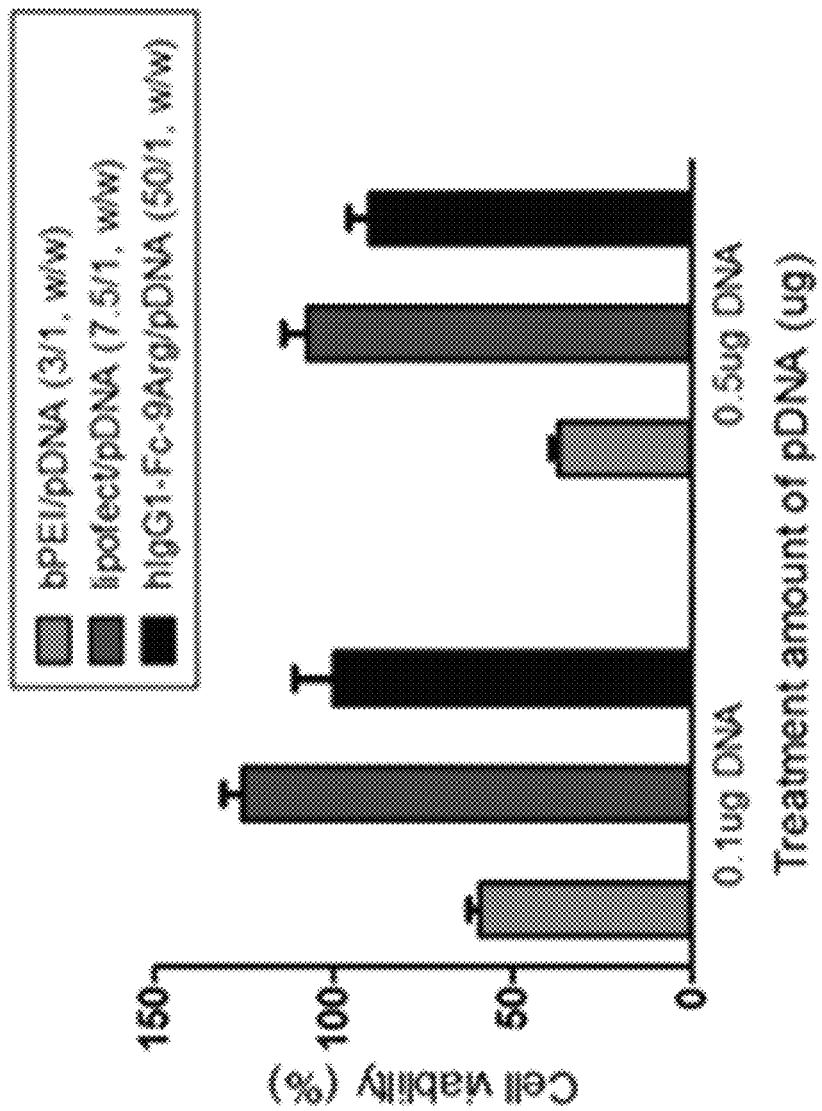
FIG. 18B shows the cytotoxicity experiment results of the hIgG1-Fc-9Arg/pDNA complex depending on the treatment concentration.

Further, as illustrated in FIG. 18B, as a result of confirming the cell toxicity of the complex bound to DNA, the hIgG1-Fc-9Arg/pDNA complex showed a relatively higher viability than that of the bPEI/DNA complex, and when treated at a concentration of 0.1 and 0.5 ug, both showed a cell viability of 90% or more, and through this, the safety of hIgG1-Fc-9Arg as a carrier was confirmed.

4-6. Confirmation of Binding Effect of hIgG1-Fc-9Arg in Organs in Animal Model

In order to confirm the delivery process of hIgG1-Fc-9Arg and the presence of specific binding to a particular organ in an animal model, after hIgG1-Fc-9Arg was orally administered to a balb/c mouse model and reacted for 1 hour and 4 hours, the mice was anesthetized with diethyl ether, and then all organs were extracted and washed three times with a PBS buffer, and fluorescence imaging analysis was performed.

Figure 19A:
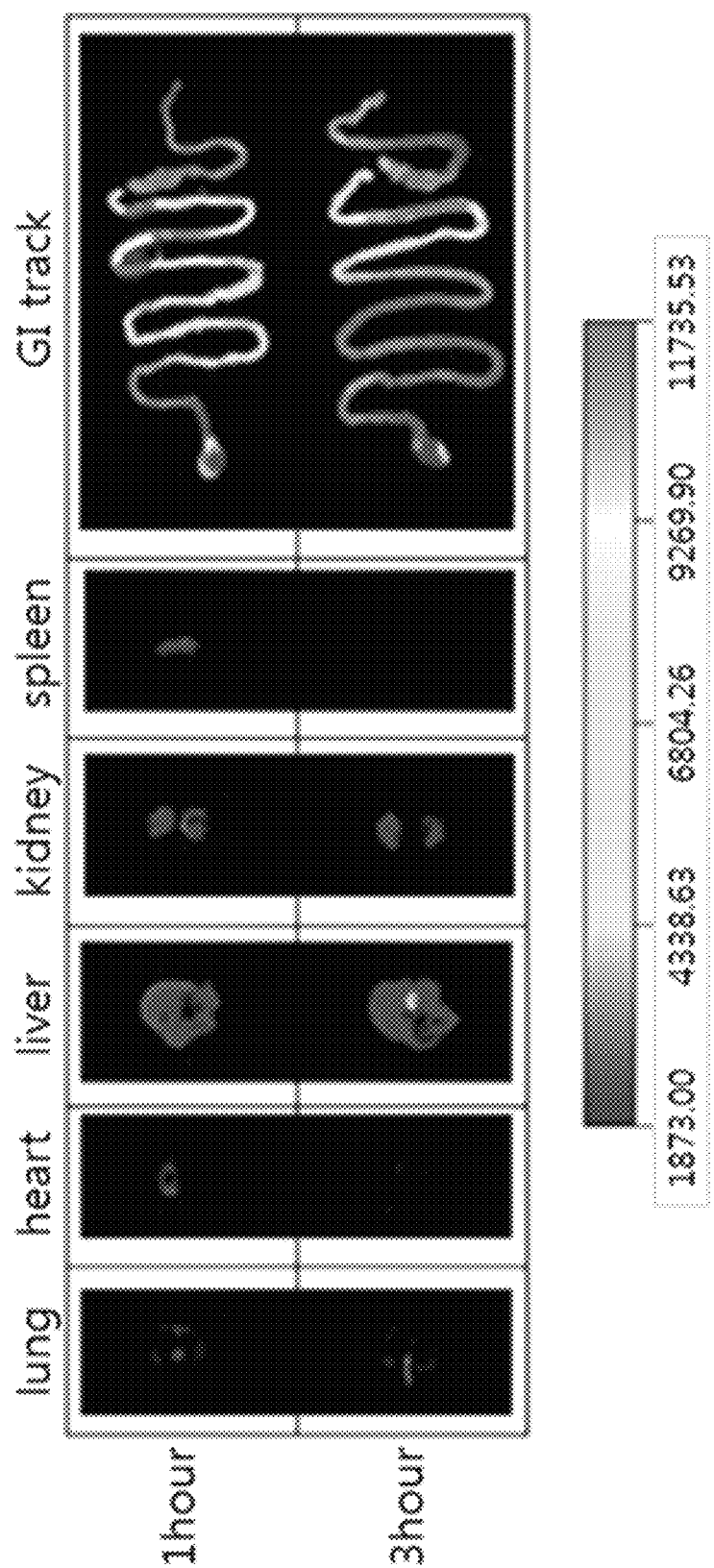
FIG. 19A is a set of imaging results showing the fluorescence intensity of FITC-hIgG1-Fc-9Arg absorbed in organs of a balb/c mouse model.

As a result, as illustrated in FIG. 19A, as a result of binding a fluorescence material FITC to hIgG1-Fc-9Arg, orally administering the hIgG1-Fc-9Arg, and then performing fluorescence imaging analysis, it could be confirmed that the IgG1-Fc-9Arg was delivered through binding to an FcRn receptor expressed in organs.

Figure 19B:
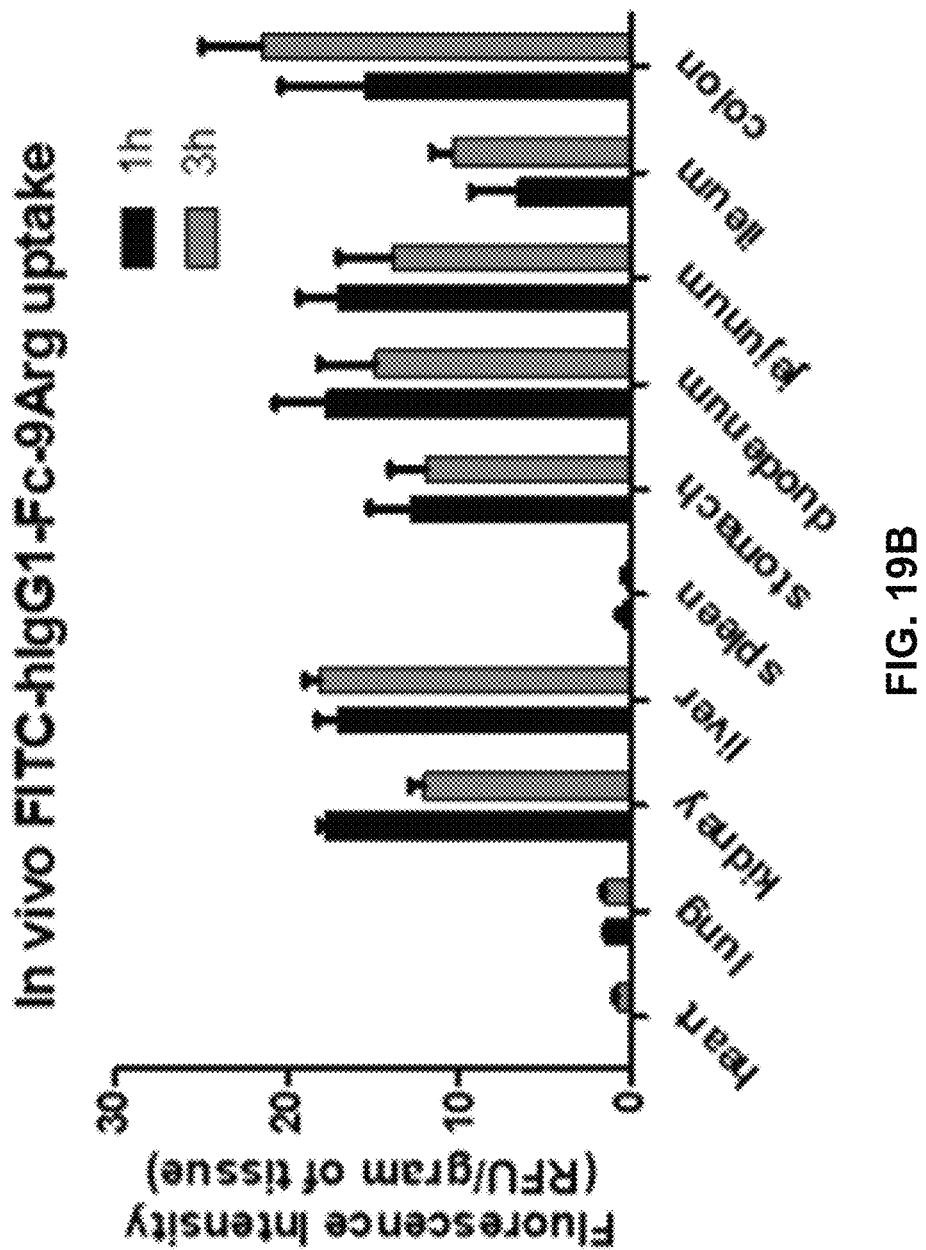
FIG. 19B shows the results of quantifying the fluorescence intensity absorbed in the organs of each mouse.

In addition, as illustrated in FIG. 19B, it was confirmed that hIgG1-Fc-9Arg was highly absorbed in the kidney, liver, stomach, duodenum, jejunum, and colon, and it could be specifically confirmed that the uptake rate was specifically increased in the colon particularly after 3 hours.

From the above results, since the gene carrier according to the present invention was absorbed in various organs, and the uptake rate was high in the intestinal organs, it was confirmed hIgG1-Fc-9Arg has excellent binding power to various organs, and thus based on this, is expected to exhibit an efficient ability when used as a gene carrier. Furthermore, it was confirmed that hIgG1-Fc-9Arg could be applied as various gene carriers in the future.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

The orally-administered gene carrier according to the present invention can stably deliver a gene by protecting the gene from the in vivo environment, and thus can be used as an effective orally-administered gene carrier, and will be usefully utilized in the field of preventing and ameliorating metabolic diseases such as diabetes mellitus or obesity, or developing a therapeutic agent, using a complex in which a GLP-1 gene is loaded into the gene carrier.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An orally-administered gene carrier comprising: an immunoglobulin Fc region; and
a linker linked to the C-terminus of the immunoglobulin Fc region,
wherein the immunoglobulin Fc region comprises a base sequence of SEQ ID NO: 4.

2. The gene carrier of claim 1, wherein the immunoglobulin Fc region is derived from any one selected from the group consisting of IgG, IgA, IgD, IgE, and IgM.

3. The gene carrier of claim 2, wherein the immunoglobulin Fc region is derived from IgG.

4. The gene carrier of claim 1, wherein the linker comprises an amino acid sequence of Arg-Arg-Arg-Arg-Arg-Arg-Arg-Arg-Arg (SEQ ID NO: 6).

5. The gene carrier of claim 1, wherein the gene carrier is prepared by being mixed with a gene at a weight ratio (w/w) of 20:1 to 150:1.

6. A method for preparing the orally-administered gene carrier of claim 1, the method comprising the following steps:
(a) constructing a recombinant expression vector comprising a nucleic acid sequence encoding a gene carrier comprising an immunoglobulin Fc region and a linker linked to the C-terminus of the immunoglobulin Fc region;
(b) transforming a host cell with the expression vector and culturing the host cell; and
(c) purifying an hIgG1-Fc-9Arg gene carrier expressed from the host cell and obtaining the hIgG1-Fc-9Arg gene carrier.

7. A method of treating metabolic diseases, comprising: administering to a subject in need thereof an effective amount of a pharmaceutical comprising the gene carrier of claim 1 and a glucagon like peptide-1 (GLP-1) gene bound to the gene carrier.

8. The method of claim 7, wherein the GLP-1 comprises a base sequence of SEQ ID NO: 5.

9. The method of claim 7, wherein the metabolic disease is selected from the group consisting of obesity, diabetes mellitus, dyslipidemia, insulin resistance, hepatic steatosis, hypercholesterolemia, and non-alcoholic fatty liver.

10. The method of claim 7, wherein the pharmaceutical composition is orally administered.

* * * * *

SEQUENCE LISTING

```
<160> NUMBER OF SEQ ID NOS: 7

<210> SEQ ID NO 1
<211> LENGTH: 95
<212> TYPE: PRT
<213> ORGANISM: Artificial Sequence
<220> FEATURE:
<223> OTHER INFORMATION: hIgG1-Fc-9Arg

<400> SEQUENCE: 1

Met Lys Trp Val Thr Phe Ile Ser Leu Leu Phe Leu Phe Ser Tyr Ser
1               5                   10                  15

Met Phe Trp Cys Gly Gly His Asp Leu Arg Leu Pro Arg Lys Lys Glu
            20                  25                  30

Met Ser Phe Glu Trp His Leu Phe Ser Ser Thr Val Val Pro Leu Gln
        35                  40                  45

Lys Ser Thr Arg His Tyr Val Leu Arg Asp Val Leu Val Met Cys Val
    50                  55                  60

Phe Ser Glu Arg Asp Arg Gly Pro Phe Arg Arg Arg Arg Arg Arg Arg
65                  70                  75                  80

Arg Arg Gly Gly Gly Ser Arg Arg Arg Arg Arg Arg Arg Arg
                85                  90                  95
```

<210> SEQ ID NO 2
<211> LENGTH: 288
<212> TYPE: DNA
<213> ORGANISM: Artificial Sequence
<220> FEATURE:
<223> OTHER INFORMATION: hIgG1-Fc-9Arg

<400> SEQUENCE: 2

```
atgaagtggg tgaccttcat ctccctgctg tttctgttct cctactccat gttctggtgc    60
ggagggcacg acctgaggct gccgaggaag aaggagatgt cgttcgagtg cacctgttc    120
tcgtccaccg tcgtccccctt gcagaagagt acgaggcact acgtactccg agacgtgttg   180
gtgatgtgcg tcttctcgga gagggacaga ggcccattc ggcggagaag aagaaggcgc    240
agaagaggcg gcggaagcag acgcaggcgg cgcagacggc ggagataa                288
```

<210> SEQ ID NO 3
<211> LENGTH: 73
<212> TYPE: PRT
<213> ORGANISM: Artificial Sequence
<220> FEATURE:
<223> OTHER INFORMATION: hIgG1-Fc

<400> SEQUENCE: 3

```
Met Lys Trp Val Thr Phe Ile Ser Leu Leu Phe Leu Phe Ser Tyr Ser
1               5                   10                  15

Met Phe Trp Cys Gly Gly His Asp Leu Arg Leu Pro Arg Lys Lys Glu
            20                  25                  30

Met Ser Phe Glu Trp His Leu Phe Ser Ser Thr Val Val Pro Leu Gln
        35                  40                  45

Lys Ser Thr Arg His Tyr Val Leu Arg Asp Val Leu Val Met Cys Val
    50                  55                  60

Phe Ser Glu Arg Asp Arg Gly Pro Phe
65                  70
```

<210> SEQ ID NO 4
<211> LENGTH: 219
<212> TYPE: DNA
<213> ORGANISM: Artificial Sequence
<220> FEATURE:
<223> OTHER INFORMATION: hIgG1-Fc

<400> SEQUENCE: 4

```
atgaagtggg tgaccttcat ctccctgctg tttctgttct cctactccat gttctggtgc    60
ggagggcacg acctgaggct gccgaggaag aaggagatgt cgttcgagtg cacctgttc    120
tcgtccaccg tcgtccccctt gcagaagagt acgaggcact acgtactccg agacgtgttg   180
gtgatgtgcg tcttctcgga gagggacaga ggcccattt                          219
```

<210> SEQ ID NO 5
<211> LENGTH: 114
<212> TYPE: DNA
<213> ORGANISM: Artificial Sequence
<220> FEATURE:
<223> OTHER INFORMATION: GLP-1

<400> SEQUENCE: 5

```
atgcgtcaac gtcgtcatgc tgaagggacc tttaccagtg atgtaagttc ttatttggaa    60
ggccaagctg ccaaggaatt cattgcttgg ctggtgaaag ccgatagtc taga           114
```

<210> SEQ ID NO 6
<211> LENGTH: 9

```
<212> TYPE: PRT
<213> ORGANISM: Artificial Sequence
<220> FEATURE:
<223> OTHER INFORMATION: linker

<400> SEQUENCE: 6

Arg Arg Arg Arg Arg Arg Arg Arg Arg
1               5

<210> SEQ ID NO 7
<211> LENGTH: 22
<212> TYPE: PRT
<213> ORGANISM: Artificial Sequence
<220> FEATURE:
<223> OTHER INFORMATION: 9 Arg-GGGS-9 Arg

<400> SEQUENCE: 7

Arg Arg Arg Arg Arg Arg Arg Arg Arg Gly Gly Gly Ser Arg Arg Arg
1               5                   10                  15

Arg Arg Arg Arg Arg Arg
            20
```